US012773104B2

(12) United States Patent
Baker

(10) Patent No.: US 12,773,104 B2
(45) Date of Patent: Oct. 27, 2026

(54) ENDOSCOPE WITH OPTICAL IMAGING SYSTEM

(71) Applicant: GYRUS ACMI, INC, Westborough, MA (US)

(72) Inventor: Charles A. Baker, Rogers, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

(21) Appl. No.: 18/777,975

(22) Filed: Jul. 19, 2024

(65) Prior Publication Data

US 2025/0025030 A1 Jan. 23, 2025

Related U.S. Application Data

(60) Provisional application No. 63/514,672, filed on Jul. 20, 2023.

(51) Int. Cl.
*A61B 1/06* (2006.01)
*A61B 1/05* (2006.01)
*A61B 5/00* (2006.01)

(52) U.S. Cl.
CPC .............. *A61B 1/0615* (2013.01); *A61B 1/05* (2013.01); *A61B 1/0661* (2013.01); *A61B 5/0066* (2013.01)

(58) Field of Classification Search
CPC ....... A61B 1/0615; A61B 1/05; A61B 1/0661; A61B 5/0066; A61B 1/00096; A61B 1/00177; A61B 1/00183; A61B 1/07
See application file for complete search history.

(56) References Cited

U.S. PATENT DOCUMENTS 6,498,948 B1 * 12/2002 Ozawa ............... G01B 9/02003 600/478
8,568,299 B2 * 10/2013 Eno ...................... A61B 1/0055 600/161
2004/0015049 A1 * 1/2004 Zaar ................... G02B 23/2484 600/101
2007/0055104 A1 * 3/2007 Kumei ............... A61B 1/00188 600/176
2008/0300456 A1 * 12/2008 Irion .................... A61B 1/0607 600/109
2009/0207412 A1 * 8/2009 Mahmood .......... G02B 23/2461 356/406

(Continued)

*Primary Examiner* — Baisakhi Roy
(74) *Attorney, Agent, or Firm* — Schwegman Lundberg & Woessner, P.A.

(57) ABSTRACT

An endoscope comprises an elongate shaft extending along an axis from a proximal end portion to a distal end portion, a video imaging device located in the distal end portion, the video imaging device including a field of view, and an optical imaging systems, e.g., an optical coherence tomography (OCT) imaging system, configured to emit light outside of the field of view. A method of imaging anatomy using an endoscope comprises inserting the endoscope into anatomy of a patient, the endoscope comprising an elongate body with a central axis, obtaining imaging with a video imaging device that includes a field of view, emitting light from a distal end portion of the endoscope outside of the field of view, obtaining reflected light from the emitted light in the multiple radial directions, and generating optical images, e.g., optical coherence tomography imaging, of the anatomy from the reflected light.

24 Claims, 10 Drawing Sheets

(56) References Cited

U.S. PATENT DOCUMENTS

| | | | | |
|---|---|---|---|---|
| 2013/0258353 | A1* | 10/2013 | Kosmecki | A61B 1/00057 356/616 |
| 2014/0357951 | A1* | 12/2014 | Muller | A61B 1/055 600/111 |
| 2018/0180868 | A1* | 6/2018 | Zhao | G02B 23/243 |
| 2020/0022570 | A1* | 1/2020 | Kennedy | A61B 1/0655 |
| 2020/0218057 | A1* | 7/2020 | Blazejewski | G02B 23/2415 |
| 2021/0186314 | A1* | 6/2021 | Hwang | A61B 1/0014 |
| 2021/0275004 | A1* | 9/2021 | Banerjee | A61B 1/00096 |
| 2021/0286187 | A1* | 9/2021 | Müller | G02B 27/14 |
| 2022/0240782 | A1* | 8/2022 | Wax | A61B 1/0638 |

* cited by examiner

ENDOSCOPE WITH OPTICAL IMAGING SYSTEM

PRIORITY CLAIM

This application claims the benefit of priority to U.S. Provisional Patent Application Ser. No. 63/514,672, filed Jul. 20, 2023, the contents of which are hereby incorporated by reference in their entirety.

TECHNICAL FIELD

The present disclosure relates generally to medical devices comprising elongate bodies configured to be inserted into incisions or openings in anatomy of a patient to provide diagnostic or treatment operations. More specifically, the present disclosure relates to endoscopes with imaging capabilities and working channels through which other instruments, such as tissue retrieval devices for biopsies, can be inserted to perform a biological matter removal and collection process.

BACKGROUND

Endoscopes can be used for one or more of 1) providing passage of other devices, e.g., therapeutic devices or tissue collection devices, toward various anatomical portions, and 2) obtaining imaging of such anatomical portions. Such anatomical portions can include gastrointestinal tract (e.g., esophagus, stomach, duodenum, pancreaticobiliary duct, intestines, colon), renal area (e.g., kidney(s), ureter, bladder, urethra) and other internal organs (e.g., reproductive systems, sinus cavities, submucosal regions, respiratory tract), and the like.

Conventional endoscopes can be involved in a variety of clinical procedures, including, for example, illuminating, imaging, detecting and diagnosing one or more disease states, providing fluid delivery (e.g., saline or other preparations via a fluid channel) toward an anatomical region, providing passage (e.g., via a working channel) of one or more therapeutic devices for sampling or treating an anatomical region, and providing suction passageways for collecting fluids (e.g., saline or other preparations) and the like.

Examples of endoscopes are described in U.S. Pat. No. 6,498,948 B1 to Ozawa et al., titled “Endoscope System.”

SUMMARY

The present disclosure recognizes that problems to be solved with conventional medical devices, and in particular endoscopes and colonoscopes used to diagnose and retrieve sample biological matter from target tissue, include, among other things, 1) the difficulty in navigating endoscopes, and instruments inserted therein, to locations in anatomical regions deep within a patient to find target tissue, 2) the difficulty in removing target tissue from anatomic locations within the patient, 3) the potential for removing the wrong tissue if the target tissue is not engaged, and 4) the potential for not removing all of the target tissue due to obstructed, misidentified or missed tissue. Such problems can be particularly present in colonoscopy procedures where target tissue, such as cancer polyps, can be located in folds or creases of tissue or behind other tissue structures, such as in the rectum, sigmoid colon and haustra (saccules) in the colon that produce the segmented shape of the colon.

The present disclosure also recognizes that problems to be solved in performing medical procedures include the ability to properly identify target tissue for removal. For example, ductal malignancies can include endometriosis and cancerous or pre-cancerous material, including carcinoma, sarcoma, myeloma, leukemia, lymphoma and mixed types of cancers.

Treatment for these ductal malignancies can involve removing the diseased tissue either as an end in itself or to perform a biopsy to determine a next course of action. As such, it is desirable to identify the ductal malignancies such that other healthy tissue in the duct or anatomy, e.g., colon, is not unnecessarily removed and to avoid additional patient intervention in a follow-up procedure to remove additional tissue. For example, it is desirable to remove all cancerous or pre-cancerous polyps from within a colon to prevent growth of the cancer.

Typically, colonoscopy relies on the use of video imaging capabilities of a colonoscope to identify the target tissue that is to be removed. Thus, locating the polyps and correctly identifying the tissue can rely heavily on surgeon skill and experience in manipulating the colonoscope within the anatomy using techniques that will find all the polyps. However, polyps can remain hidden from view of the imaging device of the colonoscope in blind spots, such as by being obstructed by anatomy of the patient, including by being located in tissue folds or behind tissue mounds, as can be produced by the haustra of the colon, or can be located in blond spots that are located outside of the field of view of the video imaging device.

Attempts have been made to incorporate imaging capabilities into endoscopes. For example, U.S. Pat. No. 6,498,948 B1 to Ozawa et al. discloses the use of Optical Coherence Tomography (OCT) in an endoscope. However, typical endoscopes incorporating OCT technology only obtain images in one radial direction relative to an axis of the endoscope, though being reciprocated in axial directions. As such, such endoscopes cannot obtain imaging in blind spots of the video imaging device located outside of the field of view of the imaging device.

The present subject matter can provide solutions to these problems and other problems, such as by providing an endoscope with optical and/or light imaging capabilities, such as an OCT imaging capability, a photoacoustic imaging capability, a diffuse optical tomography (DOT) capability, a Raman spectroscopy capability, and a super-resolution microscopy capability, in multiple radial directions relative to the central axis of the endoscope, thereby facilitating obtaining imaging in directions outside of the field of view of a video imaging device. In examples, an endoscope can comprise a rotating mirror or lens to deflect light, e.g., low-coherence light, extending axially along a light conductor in radial directions. The mirror or lens can be rotated three-hundred-sixty-degrees to project light in a complete circumference around the endoscope. In examples, the endoscope can include a plurality of light conductors arranged around the circumference of the endoscope that are curved, bent or otherwise configured to redirect axially extending light in a radial direction.

As such, the present disclosure can help solve the problems referenced above and other problems by 1) reducing the number of times a tissue retrieval device is inserted and reinserted into the anatomy, 2) providing optical and/or light imaging capabilities that can generate imaging in multiple directions to provide a complete scan or picture of an anatomic duct, 3) providing real-time optical and/or light imaging capabilities that can be used to in conjunction with a colonoscopy procedure to identify target tissue 4), providing optical and/or light imaging capabilities that can be used onboard existing endoscopes capable of performing tissue removal procedures, and 5) providing removable optical and/or light imaging capabilities that can be used to obtain preliminary imaging that can be compared to post-operative procedural results.

In an example, an endoscope can comprise an elongate shaft extending along an axis from a proximal end portion to a distal end portion, a video imaging device located in the distal end portion, the video imaging device including a field of view, and an optical imaging system configured to emit light outside of the field of view.

In another example, a method of imaging anatomy using an endoscope can comprise inserting the endoscope into anatomy of a patient, the endoscope comprising an elongate body with a central axis, obtaining imaging with a video imaging device that includes a field of view, emitting light from a distal end portion of the endoscope outside of the field of view, obtaining reflected light from the emitted light in the multiple radial directions, and generating optical images of the anatomy from the reflected light.

In an additional example, an image processing system for an endoscopy system with optical imaging capabilities for generating images of anatomy can comprise an image processor configured to receive image data from a video imaging device associated with the endoscopy system, the video imaging device including a field of view, receive imaging data from an optical imaging device associated with the endoscopy system, and generate an imaging signal for displaying an optical image for anatomy outside of the field of view of the video imaging device.

DETAILED DESCRIPTION

Figure 1:
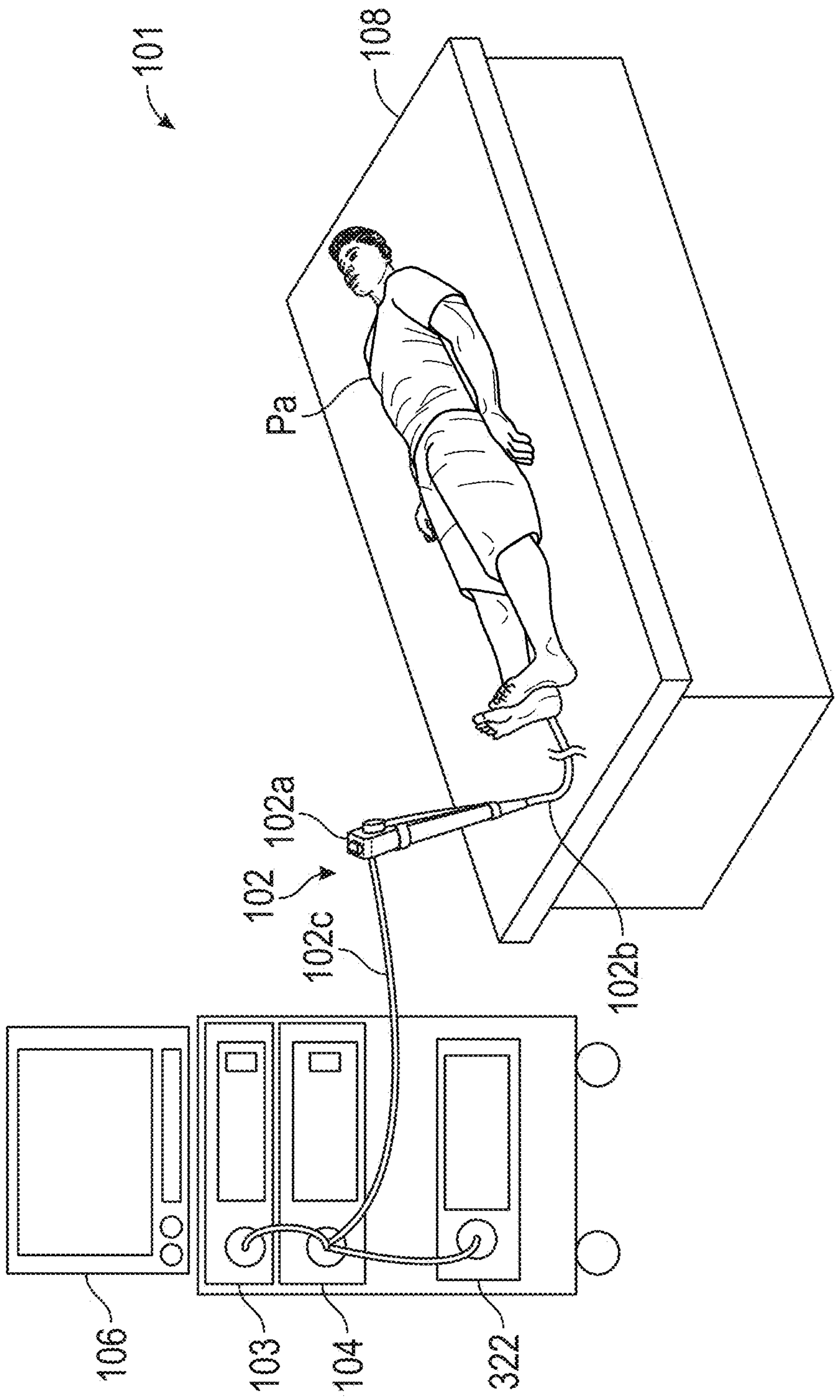
FIG. 1 is a schematic illustration of an endoscopy system comprising an imaging and control system and an endoscope, such as a colonoscope, with which an optical imaging system of the present disclosure can be used.

FIG. 1 a schematic diagram illustrating the endoscope system 101 configured for use with Optical Coherence Tomography system, or OCT system 322 (FIG. 4) according to the present disclosure. Endoscope system 101 is described with reference to an OCT imaging system, but can be used with other types of optical and light based imaging systems, such as photoacoustic imaging systems, diffuse optical tomography (DOT) systems, Raman spectroscopy systems, and super-resolution microscopy systems. Endoscope system 101 can include endoscope 102, image processing device 103, light source device 104, and monitor 106, which can be a display device. Endoscope 102 can include operation section 102*a*, flexible insertion section 102*b* and universal cable 102*c*. A physician can perform a large intestine endoscopy to patient Pa who can be lying on his back on bed 108 using endoscope system 101. However, endoscope system 101 is not limited to the configuration shown in FIG. 1, and various kinds of modifications can be made such as omitting some of these components or adding other components. For example, as described below, endoscope system 101 can include OCT system 322, as described herein.

Although FIG. 1 illustrates an example in which image processing device 103 is provided near endoscope 102, it is not limited thereto. For example, some or all of the functions of image processing device 103 can be constructed by, for example, as a server system that can be connected via a network. In other words, image processing device 103 can be implemented by cloud computing. The network as referred to herein may be a private network such as an intranet or a public communication network such as the Internet. The network may also be wired connections or wireless.

Figure 2:
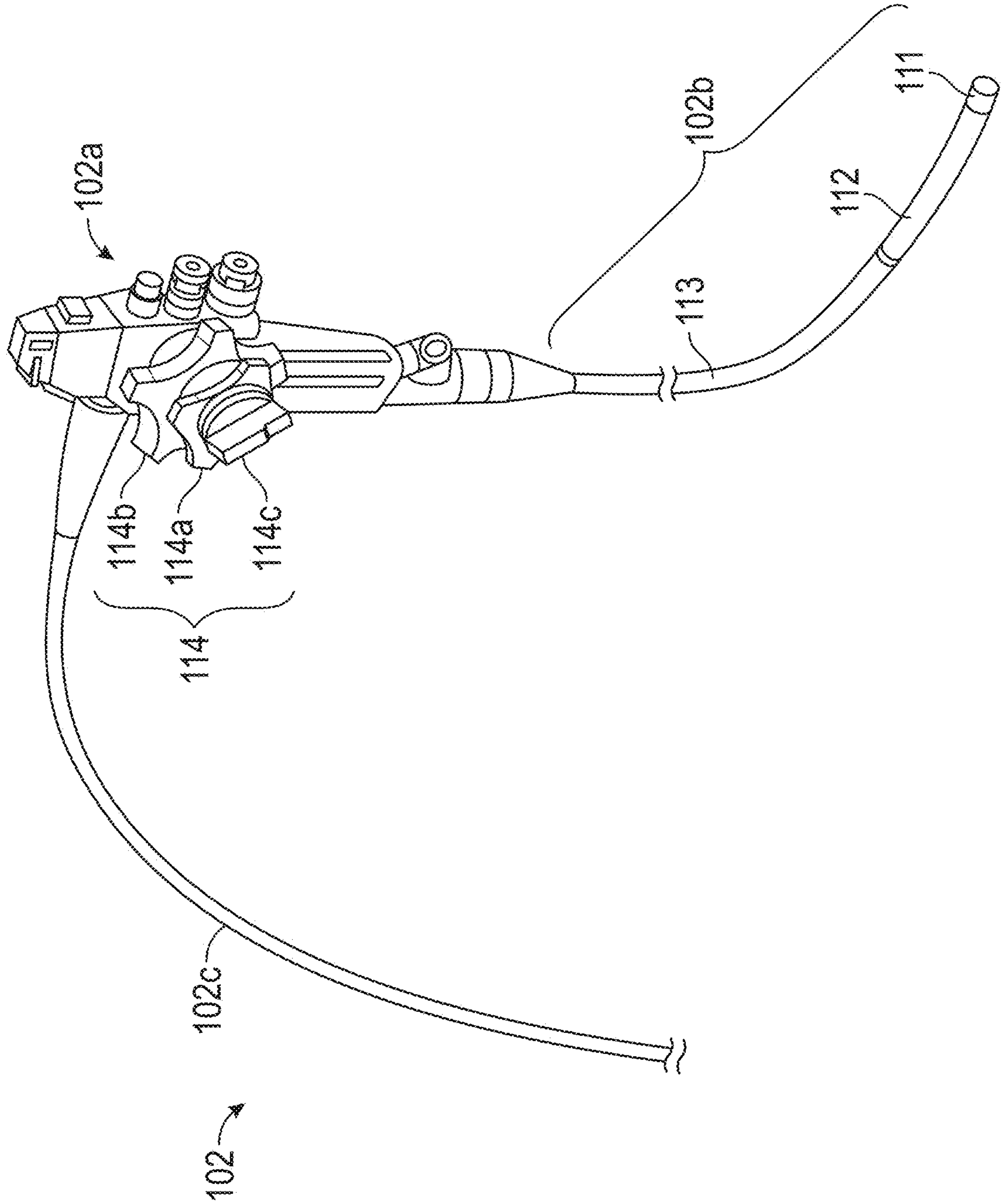
FIG. 2 is a perspective view of an example configuration of the endoscope of FIG. 1 comprising a colonoscope.

FIG. 2 is a perspective diagram of endoscope 102. Endoscope 102 can include operation section 102*a*, flexible insertion section 102*b* and universal cable 102*c* including signal lines, for example. Endoscope 102 can be a tubular insertion device for which flexible insertion section 102*b* can be inserted into a body cavity. A connector (not shown) is provided at the leading or distal end of universal cable 102*c*, and endoscope 102 can be detachably connected to light source device 104 (FIG. 1) and image processing device 103 by the connector. Endoscope 102 can comprise a colonoscope configured to be inserted into the large intestine. Furthermore, light guide 122 (FIG. 3) can be inserted into universal cable 102*c*, and endoscope 102 can emit illumination light emitted from light source device 104 from the leading or distal end of flexible insertion section 102*b* through light guide 122.

As shown in FIG. 2, flexible insertion section 102*b* can include distal end section 111, curving section 112 allowing curvature of distal end section 111, and flexible tube 113 extending from the leading or distal end to the base or proximal end of flexible insertion section 102*b*. Flexible insertion section 102*b* can be inserted into the lumen of the subject patient Pa. The base end portion of the distal end section 111 can be connected to the leading end of curving section 112, and the base end portion of curving section 112 can be connected to the leading end of flexible tube 113.

Distal end section 111 of flexible insertion section 102*b* can be the distal end section of endoscope 102, which is the hard rigid leading end.

Curving section 112 can be allowed to curve in a desired direction depending on the operation to curved operation member 114 provided in operation section 102*a*. Curved operation member 114 can include, for example, left/right curving operation knob 114*a* and an up/down curving operation knob 114*b*. When curving section 112 is curved, the position and direction of distal end section 111 is changed, and the observable portions of anatomy inside the subject patient Pa are captured within a field of view and the observable portions are illuminated by illumination light directed onto the observable portions. Curving section 112 can include a plurality of curved pieces coupled along the longitudinal axis direction of flexible insertion section 102*b*. Thus, a physician can observe anatomy of patient Pa, such as the large intestine, by inducing curvature of curving section 112 in various directions while pushing flexible insertion section 102*b* into the large intestine or pulling it away from the large intestine.

Left/right curving operation knob 114*a* and up/down curving operation knob 114*b* can cause an operation wire, e.g., a pull wire or steering wire, inserted into flexible insertion section 102*b* to pull and relax in order to curve curving section 112. Curved operation member 114 can further include fixing knob 114*c* to fix or lock the position of curving section 112. Note that operation section 102*a* can also be provided with various operation buttons such as a release button or an air supply and water supply button in addition to curved operation member 114 to allow for the flow or air and water through one or more of operation section 102*a*, flexible insertion section 102*b* and universal cable 102*c*. Universal cable 102*c* can additionally be used to transmit optical imaging signals, e.g., OCT imaging signals, and light signals to and from OCT system 322 or another optical system.

Flexible tube 113 is flexible, and thus can bend in response to external force. Flexible tube 113 can be a tubular member extending from operation section 102*a*.

Image sensor 115, which is an imaging device such as a CMOS sensor or camera, can be provided in distal end section 111 of flexible insertion section 102*b*. The observable portions in the large intestine illuminated by the illumination light of light source device 104 can be captured by image sensor 115. That is, image sensor 115 can be provided in distal end section 111 of flexible insertion section 102*b* and can comprise an imaging section for capturing video images inside the subject patient Pa. Image signals obtained by image sensor 115 can be supplied to image processing device 103 via signal lines within universal cable 102*c*. Note that the position provided with image sensor 115 is not limited to distal end section 111 of flexible insertion section 102*b* for end-viewing. For example, image sensor 115 may be provided at a position on the base end side rather than distal end section 111 or may be provided on the side of flexible insertion section 102*b* for side-viewing.

Image processing device 103 can be a video processor to perform predetermined image processing to received image signals from image sensor 115 and to generate the captured images. The video signals of the generated captured images can be output from image processing device 103 to monitor 106, and the live captured images can be displayed on monitor 106. A physician performing a procedure or examination can insert distal end section 111 of flexible insertion section 102*b* through the anus of the patient Pa and observe inside the large intestine of the patient Pa.

Light source device 104 is a light source device configured to emit light to facilitate observation of the observable portion of the anatomy of patient Pa. Light source device 104 can be configured to emit visible light, such as white light, or other types of light for special viewing modes, such as blue light or other light. Light source device 104 can include LED lights, Xenon lights, incandescent light bulbs and the like.

Figure 3:
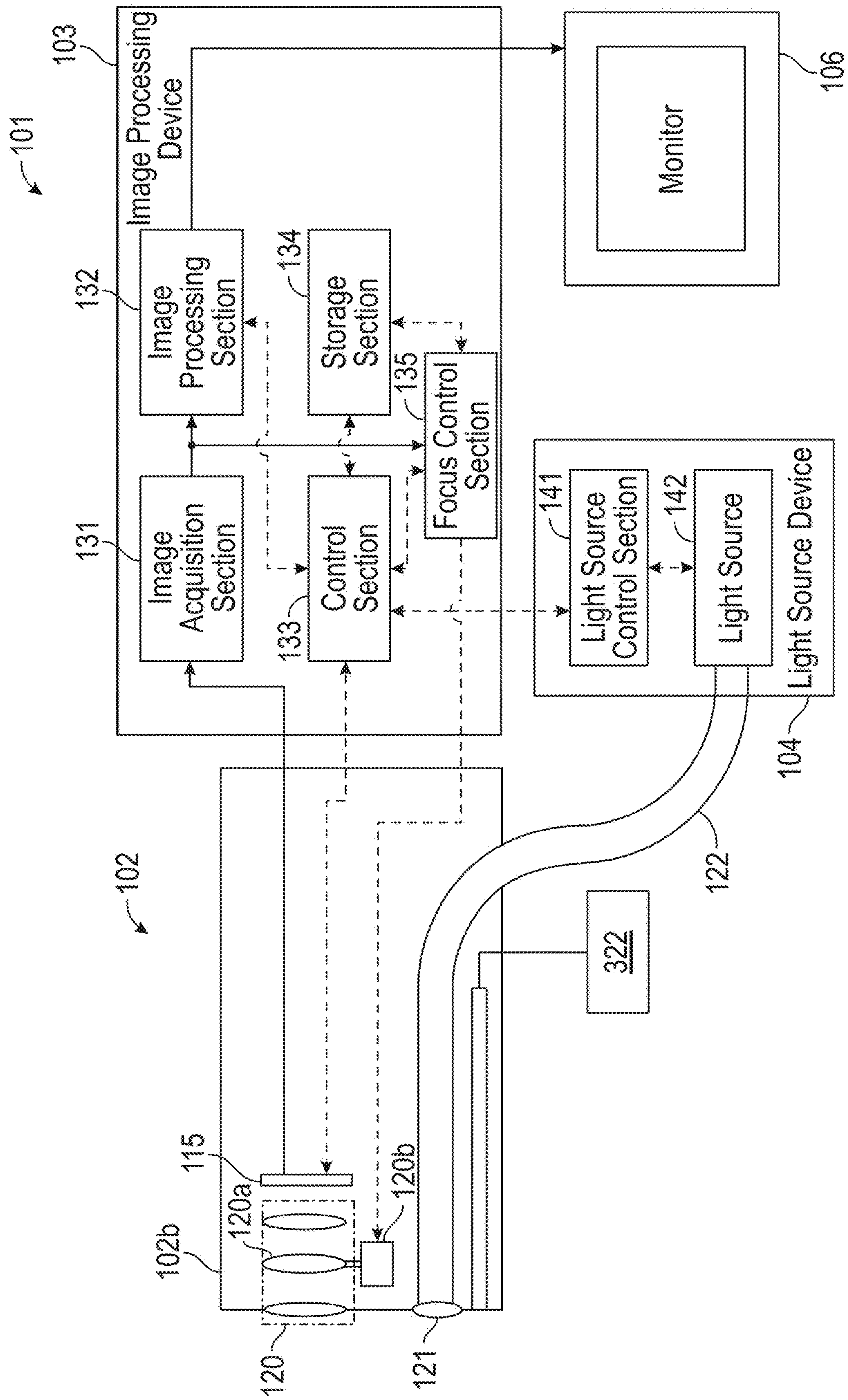
FIG. 3 is a schematic illustration of an example configuration of various sections of the endoscopy system of FIG. 1.
Figure 4:
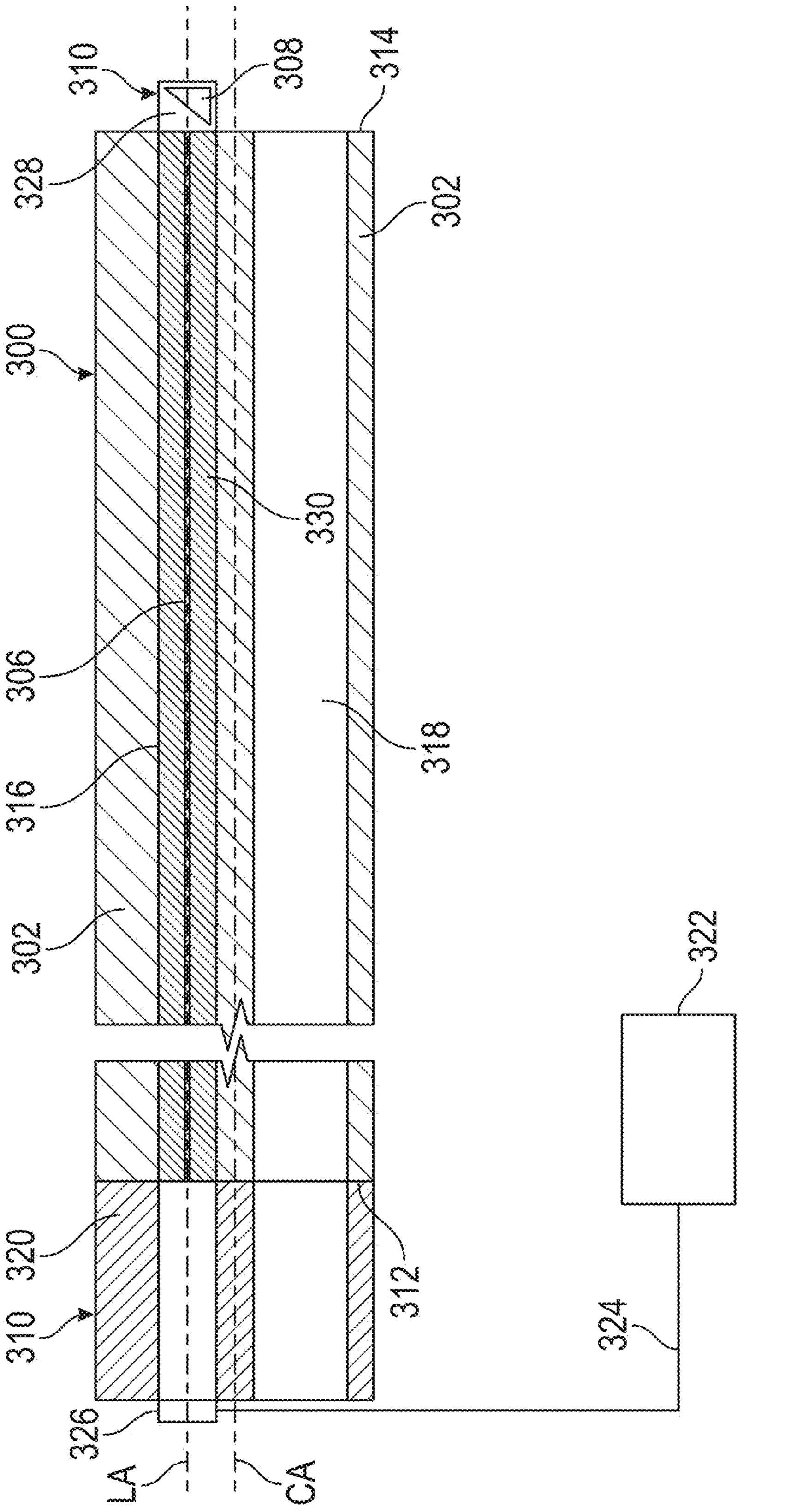
FIG. 4 is a schematic illustration of an endoscope comprising an optical imaging apparatus with a light conductor and a rotating mirror structure for conveying an optical imaging signal in multiple radial directions.

As described in greater detail below, endoscope system 101 can also include an optical imaging system, such as OCT system 322 (FIGS. 1, 3 and FIG. 4). The optical imaging system can be configured to generate three-dimensional imaging of an internal duct of the patient in a three-hundred-sixty-degree field-of-view using endoscope 102 using various optical imaging techniques, such as optical coherence tomography and the like.

FIG. 3 is a schematic diagram illustrating a configuration of each section of endoscope system 101 including image processing device 103. Image processing device 103 can perform the image processing and the overall system control. Image processing device 103 can include image acquisition section 131, image processing section 132, control section 133, storage section 134, and focus control section 135. Flexible insertion section 102*b* can include subject light acquisition section 120, image sensor 115, illumination lens 121, and light guide 122. Subject light acquisition section 120 is specifically an objective optical system including one or more lenses. For example, subject light acquisition section 120 can include focus lens 120*a*, which can be driven by actuator 120*b*.

Light guide 122 can guide the illumination light emitted from light source device 104 to the leading end of flexible insertion section 102*b*. Illumination lens 121 can illuminate or irradiate the observable portions of patient Pa, e.g., the subject, with the illumination light guided by light guide 122. Subject light acquisition section 120 acquires the subject light, which is light reflected from the subject. Subject light acquisition section 120 can include focus lens 120*a*, which can change a focus object-position depending on the position of focus lens 120*a*. Actuator 120*b* can drive focus lens 120*a* based on an instruction from focus control section 135. The focus object-position as referred to herein represents the position of the object when a system comprising a lens system, an image plane, and an object is in focus. For example, when the image plane is the plane of the image sensor, the focus object-position represents the position of the subject that is ideally in focus in the captured images when the image sensor is used to capture the subject images through the above lens system.

Image sensor 115, which is the imaging section, may be a monochrome sensor or a sensor with a color filter. The color filter may be a widely known Bayer filter, a complementary color filter, or any other filters. The complementary color filter is a filter including each color filter with cyan, magenta, and yellow.

Image processing device 103 can be configured by hardware as described below. The hardware can include at least one of the circuits processing the digital signals or the circuits processing the analog signals. For example, the hardware can be configured by one or more circuit devices implemented on a circuit substrate or one or more circuit elements. The one or more circuit devices are, for example, such as an integrated circuit (IC) or field-programmable gate arrays (FPGA). The one or more circuit elements are, for example, such as a resistor or a capacitor.

Image processing device 103 can also be implemented by a processor as described below. Image processing device

103 can include memory to store information and the processor to operate based on the information stored in the memory. The information can be, for example, a program and various data. The processor can include the hardware. The processor can use various processors, such as a Central Processing Unit (CPU), a Graphics Processing Unit (GPU), a Digital Signal Processor (DSP). The memory can be semiconductor memory such as Static Random Access Memory (SRAM), Dynamic Random Access Memory (DRAM), or the register, or a magnetic memory device such as a Hard Disk drive (HDD), or an optical memory device such as an optical disk device. For example, the memory can store computer-readable instructions that the processor can execute to cause the functions of each section of image processing device 103 to be implemented. Image processing device 103 can include the specific sections illustrated in FIG. 3, such as image acquisition section 131, image processing section 132, control section 133, storage section 134 and focus control section 135. The instructions as referred to herein may be a set of instructions configuring the program, or the instructions instructing the hardware circuit of the processor to operate.

Each section of image processing device 103 can also be implemented as a module of the program operating on the processor. For example, control section 133 can be a control module for controlling each section of the endoscope system 101. Specifically, control section 133 can be a control module for controlling a turning mechanism and/or an advancing/retreating mechanism used to control the shape and position of flexible insertion section 102*b*.

The program for implementing the processing performed by each section of image processing device 103 can be stored in an information storage device, which is, for example, a computer-readable medium. The information storage device can be implemented by, for example, an optical disk, a memory card, HDD, or semiconductor memory. The semiconductor memory can be, for example, ROM. In examples, control section 133 of image processing device 103 can perform various processing based on the program stored in the information storage device. That is, the information storage device stores the programs to make the computer function as each section of image processing device 103. The computer is a device comprising an input device, a processing section, a storage part, and an output part. The program is a program for causing the computer to perform the processing of each section of image processing device 103.

Image acquisition section 131 can acquire the captured image output sequentially from the imaging section and output the acquired captured images to image processing section 132 and focus control section 135. The acquired images are output sequentially to image processing section 132 and focus control section 135. Image processing section 132 can perform various image processing on the captured images, such as white balance processing, demosaicing (synchronization) processing, noise reduction processing, color conversion processing, tone conversion processing, and contour enhancement processing, and outputs the processed captured images sequentially to monitor 106. Control section 133 can perform input and output of various control signals.

Focus control section 135 can control focus lens 120*a* based on the captured images. Focus control section 135 can controls focus lens 120*a* based on, for example, the known contrast AF. For example, focus control section 135 can control focus lens 120*a* based on the known contrast AF. However, AF is not an essential component of endoscope system 101 and thus focus control section 135 can be omitted.

Light source device 104 can include light source control section 141 and light source 142. Light source control section 141 can control the light intensity of light source 142 in accordance with the target light intensity of the light source sequentially output from control section 133. Light source 142 can emit the illumination light. Light source 142 can be a xenon light source, a light emitting diode (LED), or a laser light source. Light source 142 can also be other light sources, and thus the light emitting method is not limited.

In examples, endoscope system 101 can be configured according to Pub. No. US 2022/0400931A1 to Hane, titled "Endoscope system, method of scanning lumen using endoscope system, and endoscope," the entire contents of which are hereby incorporated by this reference.

It can be difficult to locate and identify biological matter that is to be removed from the patient, e.g., target tissue. In examples, the target tissue can be cancer or pre-cancerous polyps. It can be difficult to view the target tissue due to multiple reasons, including the presence of a tissue retrieval device in the line of sight of the colonoscope camera. Furthermore, image sensor 115 may not always be able to obtain line-of-sight of all target tissue due to the target tissue being obscured by other tissue. This thereby makes collection of non-desirable, e.g., non-cancerous, material a possibility. Furthermore, the potential for leaving behind target tissue that is desired to be removed increases. However, with the systems and devices of the present disclosure, locating and identifying target tissue is more readily accomplished using the optical imaging capabilities of the present disclosure, such as optical coherence tomography. For example, endoscope system 101 can comprise OCT system 322 that can obtain optical coherence tomography imaging of anatomy in the patient from distal end section 111 of endoscope 102. However, as mentioned, other types of optical imaging systems can be used with the present disclosure, such as photoacoustic imaging systems, diffuse optical tomography (DOT) systems, Raman spectroscopy systems, and super-resolution microscopy systems. As such, OCT system 322 or another optical imaging system can be configured to emit light waves that can bounce of the anatomy of patient Pa at different depth to construct a three-dimensional profile of the anatomy to facilitate identification and location of target tissue, as discussed in greater detail below with reference to FIG. 10. OCT imaging can comprise an example of interferometry wherein short-coherence length light is used to produce imaging with micrometer-level depth resolution. OCT imaging can be performed using a super-luminescent diode (SLD). Photoacoustic imaging can comprise a technique wherein non-ionizing laser pulses are used to produce images. The non-ionizing laser pulses can produce ultrasonic emission by causing transient thermoelastic expansion from heat generated therefrom. Diffuse optical tomography or imaging can utilize near-infrared light to observe spatial-temporal variation in light absorption and scattering properties of tissue. Raman spectroscopy can utilize monochromatic light in visible, near infrared and near ultraviolet range to induce vibration in tissue that can shift the laser energy. Super-resolution microscopy can include stimulated emission depletion (STED) microscopy, structured illumination microscopy (SIM), and stochastic optical reconstruction microscopy (STORM)/photoactivation localization microscopy (PALM).

Figure 5:
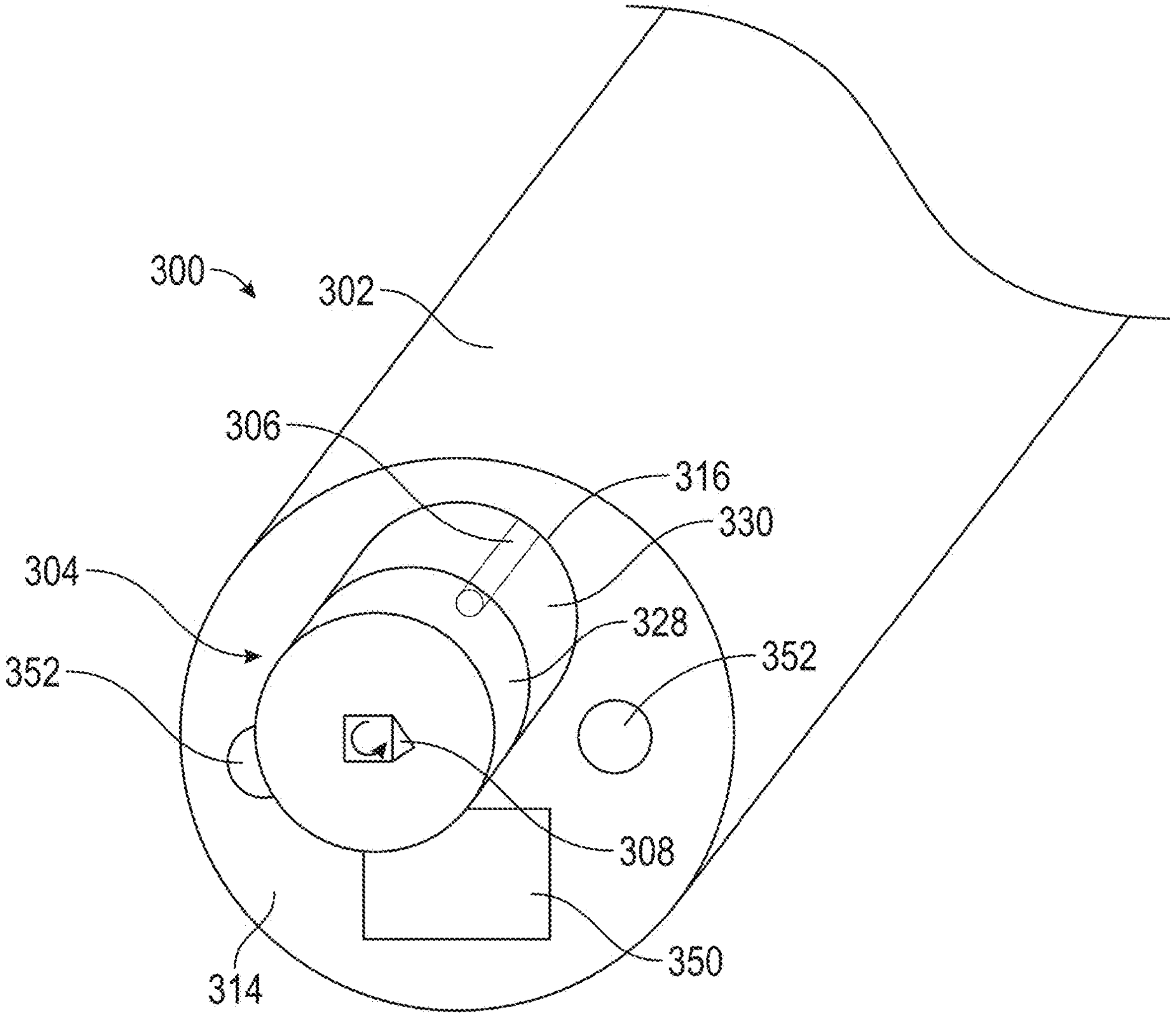
FIG. 5 is a perspective view of the distal end of the endoscope of FIG. 4 taken from a distal direction showing the optical imaging apparatus extending from a shaft of the endoscope.

FIG. 4 is a schematic illustration of endoscope 300 comprising elongate body 302 that includes OCT imaging apparatus 304, wherein OCT is an abbreviation for Optical Coherence Tomography. FIG. 5 is a perspective view of distal portion 314 of endoscope 300 of FIG. 4 taken from a distal direction showing OCT imaging apparatus 304 extending from elongate body 302 of endoscope 300. In examples, endoscope 300 can be configured as a colonoscope, such as endoscope 102 of FIG. 1, which can be used to image and collect biological matter using a biopsy device or tissue removal device. FIGS. 4 and 5 are discussed concurrently.

OCT imaging apparatus 304 can comprise light-conducting element 306 and light-bending element 308. Endoscope 300 can further comprise controller 310. The components illustrated in FIG. 4 are not necessarily drawn to scale. Elongate body 302 can comprise a shaft extending between proximal portion 312 at the interface with controller 310 and distal portion 314 at the interface with OCT imaging apparatus 304. Lumen 316 and working channel 318 can extend between proximal portion 312 and distal portion 314.

Elongate body 302 can comprise an elongate shaft member configured to allow endoscope 300 to be inserted into anatomy of a patient. Elongate body 302 can be inserted into an orifice or an incision in the epidermis of a patient, through a body cavity of the patient and into an organ, such as a colon. Thus, it is desirable for the diameter or cross-sectional shape of elongate body 302, as well as components attached thereto, to be small to facilitate minimally invasive surgical procedures. OCT imaging apparatus 304 can thus be incorporated into elongate body 302, as opposed to being attached to the exterior of elongate body 302, to minimize the size impact on endoscope 300. However, in additional examples, OCT imaging apparatus 304 can be configured to be attached to the exterior of elongate body 302, as discussed below. Elongate body 302 can be axially rigid along central axis CA, but resiliently bendable in radial directions, and formed from a metal or plastic material.

Elongate body 302 is illustrated as including light-conducting element 306 within lumen 316. In examples, lumen 316 can comprise a dedicated channel for light-conducting element 306 and working channel 318 can comprise an open channel for receiving other instruments, with other passages being provided in elongate body 302 for receiving wiring and cables for imaging sensor 350 and illumination lenses 352 (FIG. 5). Elongate body 302 can additionally include other elements and components such as cables, tubes and the like to facilitate other capabilities, such as imaging, insufflation and irrigation. As such, endoscope 300 can comprise a fully functioning colonoscope with additional imaging capabilities provided by OCT imaging apparatus 304 or another type of optical imaging apparatus.

In examples, endoscope 300 can be provided as a dedicated imaging device without an instrument working channel such that working channel 318 can be used for wiring and cables for imaging sensor 350 and illumination lenses 352 (FIG. 5).

In additional examples, OCT imaging apparatus 304 or another type of optical imaging apparatus can be configured as a standalone device or attachment system to be inserted into a working channel of a colonoscope to be used alternatively with another instrument, such as a biopsy device. In other examples, a standalone OCT imaging apparatus 304 or another type of optical imaging apparatus can be configured to extend along an exterior of elongate body 302, such as by structure 330 extending alongside elongate body 302 to connect to cap 328 positioned in front of elongate body 302.

Distal portion 314 can comprise functional components, such as imaging components and lighting components. In particular, as shown in FIG. 5, endoscope 300 can comprise imaging sensor 350 and illumination lenses 352, to facilitate navigation of endoscope 300 through the anatomy. Light-bending element 308 is illustrated as being positioned distally of imaging sensor 350 (FIG. 5). However, light-bending element 308 can be positioned proximally of imaging sensor 350. In examples, imaging sensor 350 can be configured with a field of view, such as in a distal direction for end-viewing, and light-bending element 308 can be oriented to project light outside of the field of view, such as in multiple radial directions proximal of the field of view by projecting light backwards. However, imaging sensor 350 can be configured in a side-viewing orientation and light-bending element 308 can be oriented to project light outside of the field of view of a side-viewing imaging sensor.

Controller 310 can comprise a device located at proximal portion 312 of elongate body 302 and can be configured to operate components of elongate body 302 and components attached thereto, such as OCT imaging apparatus 304, other types of optical imaging apparatuses and other elements of endoscope 300. Controller 310 can comprise a handpiece or handle and can be shaped as a knob, a pistol grip, a shaft, a handlebar or the like. Controller 310 can include various control knobs, buttons and the like for operating steering capabilities of elongate body 302, such as by tensioning and loosening pull wires within elongate body 302.

Controller 310 can comprise socket 320 for receiving light-conducting element 306. Socket 320 can be configured to connect light-conducting element 306 to OCT system 322 or optical tomographic imaging system 501 of FIG. 10. OCT system 322 can include cable 324 and plug 326. Plug 326 can be used to connect controller 310 to OCT system 322. Cable 324 can include appropriate wiring for conveying imaging, light and communication signals between OCT system 322 and controller 310. Controller 310 can include various control knobs, buttons and the like for operating OCT system 322. Controller 310 can be configured similarly as any of the controllers described herein, such as operation section **102*a* of FIG. 2**.

Light-conducting element 306 can be a light transmitter configured to conduct light waves to perform optical imaging including OCT imaging, such as an optical fiber. The light waves can originate at OCT system 322. Light-conducting element 306 can be used to conduct low-coherence light and other types of light from OCT system 322 and controller 310 to distal portion 314 and cap 328 via cable 324 and plug 326. As such, low-coherence light and other types of light from OCT system 322 can be transmitted to distal portion 314 to provide light for imaging anatomy. In examples, light-conducting element 306 can comprise a fiber or filament capable of transmitting light and in particular low-coherence light. Light-conducting element 306 can comprise a medium for transmitting light from OCT system 322 to cap 328.

In examples, light-conducting element 306 can be made from silica, fluorozirconate, fluoroaluminate, chalcogenide glasses, and crystalline materials such as sapphire. Cable 324 can comprise an extension of light-conducting element 306 and can be fabricated from the same material as light-conducting element 306. In examples, light-conducting element 306 and cable 324 can comprise fiber optic cables. In examples, the fiber optic cables can comprise glass and plastic fibers jacketed with one or more protective and reflective coatings. In examples, light-conducting element 306 can include a circular cross-sectional area with a diameter in the range of approximately 250 microns (μm/1×10$^{-6}$ meter) to 500 microns (μm/1×10$^{-6}$ meter). Additionally, in examples using thulium fiber laser modules, light-conducting element 306 can include a circular cross-sectional diameter in the range of approximately 50 microns to 150 microns. As discussed with reference to FIGS. 8 and 9, various examples of the OCT imaging endoscopes described herein can include a plurality of light-conducting elements that emit light in different directions, whereby a small diameter of the light-conducting elements is desirable.

Endoscope 300 can comprise cap 328 located at distal portion 314 of elongate body 302. Cap 328 can include light-bending element 308. Cap 328 can be disposed adjacent the terminal end of light-conducting element 306 to direct light emitting therefrom onto light-bending element 308. In examples, cap 328 can comprise any suitable body for transmitting light, such as a glass or plastic body of transparent material. As discussed with reference to FIGS. 6 and 7, cap 328 can comprise a lens to allow light to pass into light-bending element 308 and out of cap 328. Light-bending element 308 can comprise a lens, mirror, prism or the like. Light-bending element 308 can be configured to turn light extending through light-conducting element 306 parallel to center axis CA of elongate body 302 along light axis LA.

Cap 328 can be located at the end of elongate body 302 to seal-off lumen 316 from the environment of elongate body 302. In examples, as shown in FIG. 4, cap 328 can be approximately the same diameter as lumen 316. However, cap 328 can be larger or smaller than lumen 316 in other configurations. In examples, lumen 316 can be partially or wholly filled with a material that is located around, and may partially or wholly surround light-conducting element 306. For example, light-conducting element 306 is located in structure 330, and can be embedded in, in contact with, or otherwise surrounded by structure 330. Structure 330 can comprise a body of rigid or flexible material to protect light-conducting element 306. In examples, structure 330 can be slightly smaller than the diameter of lumen 316 to allow OCT imaging apparatus 304 to be removed from elongate body 302. Thus, cap 328 along with light-bending element 308 and socket 320 can be withdrawn from elongate body 302 and controller 310.

As discussed herein, cap 328 can be configured to rotate to orient light-bending element 308 in different orientations about light axis LA to project low-coherence light for OCT imaging and other types of light for other types of imaging in a three-hundred-sixty-degree ring about endoscope 300.

Figure 6:
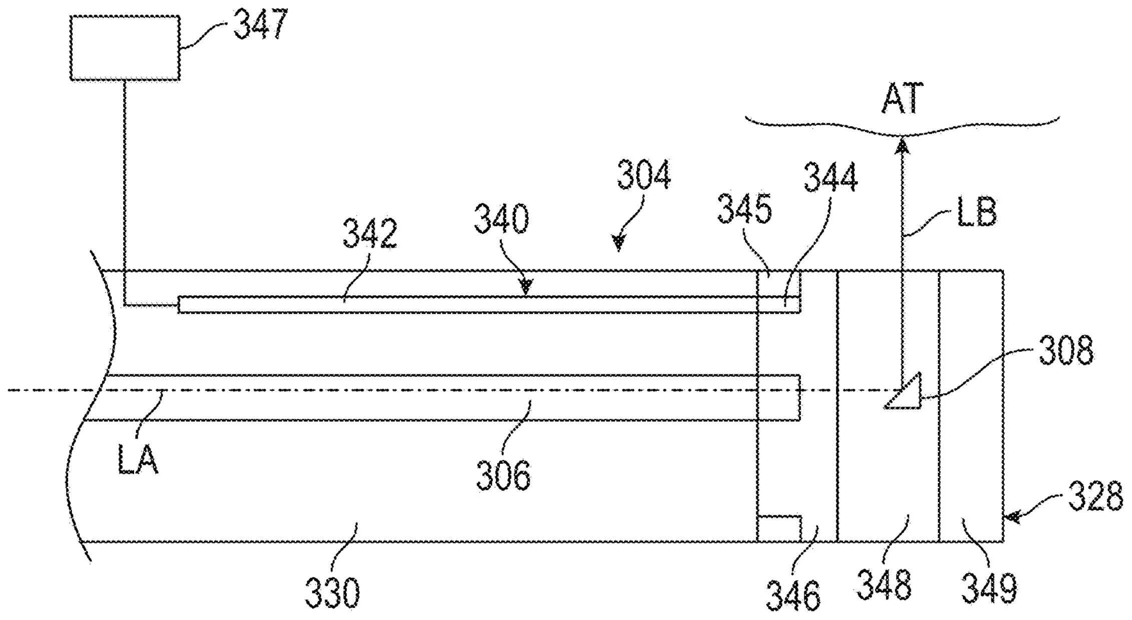
FIG. 6 is a close-up, side, cross-section view of the optical imaging apparatus of FIG. 4 showing a cylinder ring lens with the rotating mirror.
Figure 7:
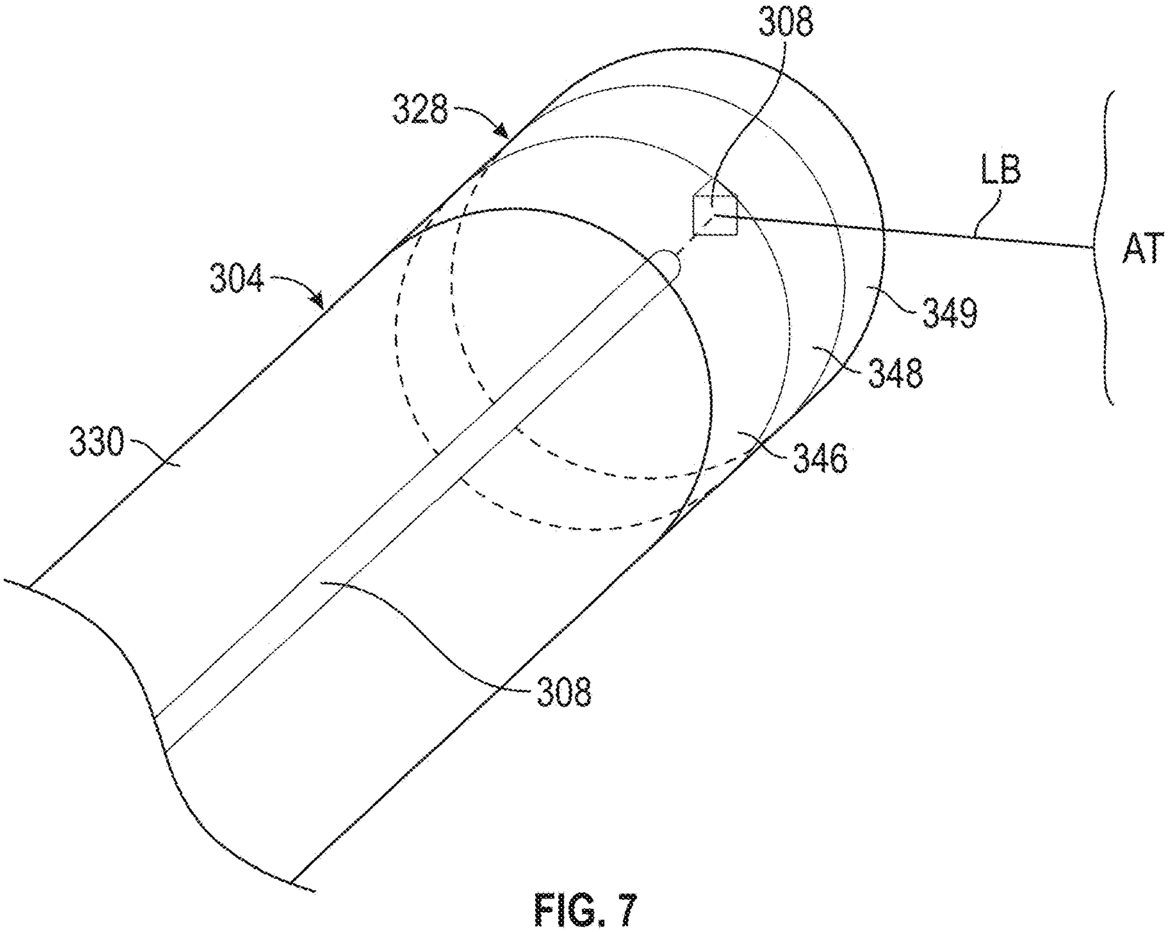
FIG. 7 is a perspective view of the distal end of the optical imaging apparatus of FIG. 6 taken from a proximal direction showing the rotating mirror structure deflecting light toward anatomic tissue.

FIG. 6 is a close up, side, cross-section view of OCT imaging apparatus 304 of FIGS. 4 and 5 showing cap 328 with light-bending element 308. FIG. 7 is a perspective view of the distal end of OCT imaging apparatus 304 of FIGS. 4 and 5 taken from a proximal direction showing cap 328 with light-bending element 308 deflecting light beam LB toward anatomic tissue AT. FIGS. 6 and 7 are discussed concurrently. Light beam LB can comprise short-coherence length light, laser light, non-ionizing laser light, LED light, near-infrared light, monochromatic light, visible light, near infrared light, near ultraviolet light and others.

Figure 10:
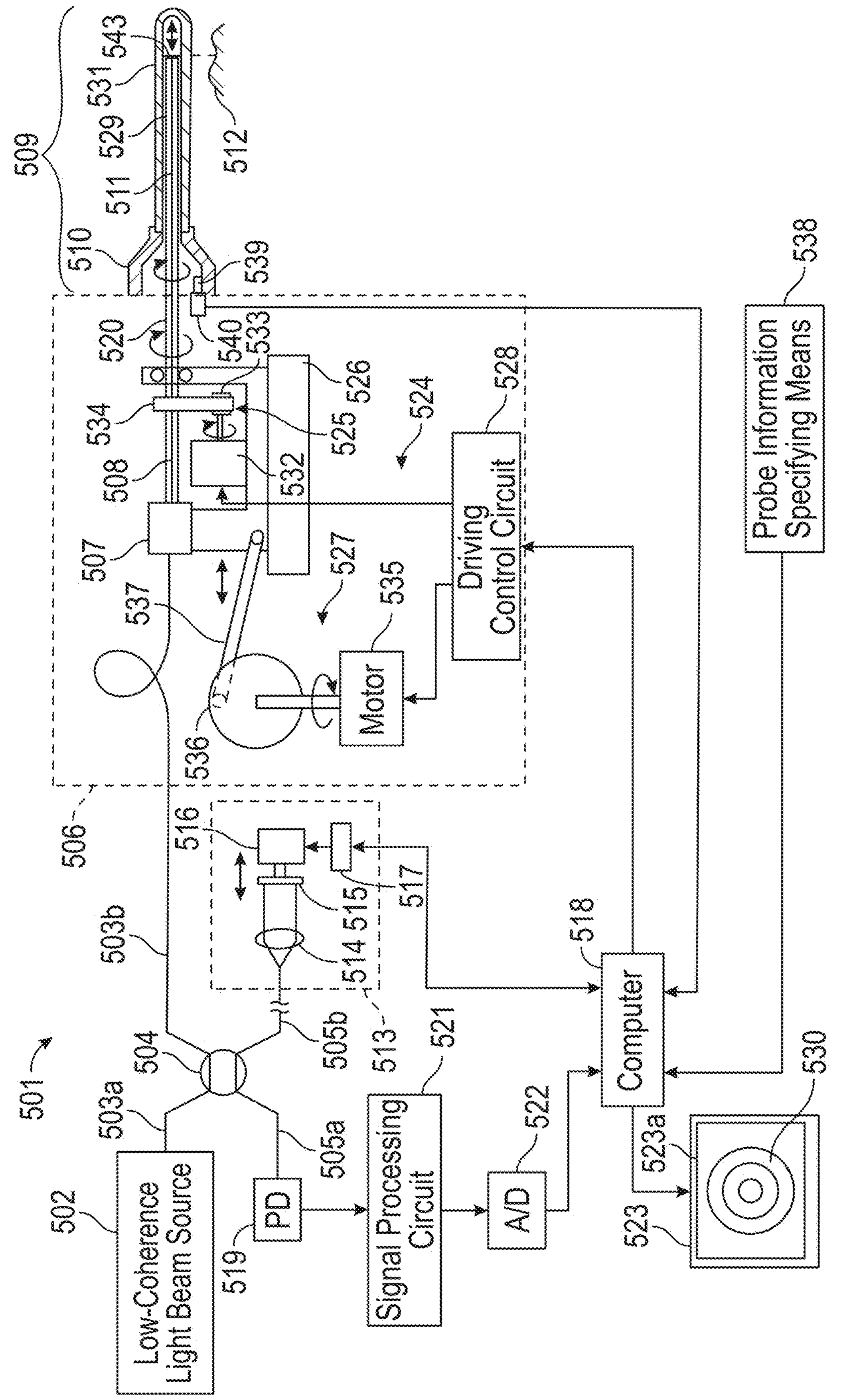
FIG. 10 is a schematic diagram of an optical imaging system suitable for use with the systems and devices of the present disclosure.

OCT imaging apparatus 304 can include drive system 340 configured to rotate cap 328. Drive system 340 can comprise shaft 342 and pinion gear 344. Cap 328 can include ring gear 346, lens 348 and end plate 349. Shaft 342 can connect to a motor, such as motor 532 (FIG. 10).

Ring gear 346 can be rotatably mounted to structure 330 by any suitable means. For example, ring gear 346 and structure 330 can include interlocking flanges and grooves that prevent axial movement therebetween but permit relative rotation therebetween. In examples, ring gear 346 can be annular or ring-shaped to allow light-conducting element 306 to extend close to lens 348 and to allow light emitting from light-conducting element 306 to pass into lens 348.

Drive system 340 can comprise a system for imparting rotation of ring gear 346 about central axis CA. Shaft 342 can comprise an elongate body configured to receive a rotational input to rotate pinion gear 344. In examples, shaft 342 can comprise a flexible drive shaft, such as a cable, that can extend loosely through a lumen within structure 330. A proximal end of shaft 342 can connect to a motor that drives shaft 342 in a rotational manner. In examples, a dedicated motor 347. In examples, shaft 342 can be driven by motor 532 or motor 535 (FIG. 10). Pinion gear 344 can engage with inward-facing gear teeth 345 of ring gear 346. Thus, rotation of motor 347, can cause rotation of shaft 342, which can rotate pinion gear 344, which can rotate ring gear 346, which can rotate lens 348. Lens 348 can be rotated in a circumferential direction relative to the center axis CA of elongate body 302 to obtain optical imaging, including OCT imaging, about the complete circumference of elongate body 302.

Lens 348 can comprise a light-transmitting body to allow light from light-conducting element 306 to pass into lens 348 and contact light-bending element 308 and light deflected by light-bending element to pass out of lens 348. In examples, lens 348 can comprise a transparent polycarbonate body that can support light-bending element 308.

Light-bending element 308 can comprise a body configure to deflect light emitted from light-conducting element 306 off light axis LA. In examples, light-bending element 308 can be configured to deflect light ninety-degrees directly radially outward of endoscope 300. In examples, light-bending element 308 can be configured to direct light axially forward or rearward, e.g., distally or proximally, of light-bending element 308. In examples, light-bending element can include a mirrored surface to deflect light from light-conducting element 306, as illustrated. In additional examples, light-bending element 308 can comprise a triangular prism wherein light can enter a surface tangent to light-conducting element 306, impact an angled surface, and pass through another surface parallel to light-conducting element 306. For example, light-bending element 308 can comprise a right-angle prism having a light reflecting surface angled forty-five degrees relative to light axis LA, although prisms with light reflecting surfaces at other angles can be used. In examples, light-bending element 308 can comprise a glass substrate with a coating of silver or aluminum. For example, light-bending element 308 can comprise a mirror having a light reflecting surface angled forty-five degrees relative to light axis LA, although mirrors with light reflecting surfaces at other angles can be used. As light-bending element 308 is rotated about light axis LA by rotation of lens 348 from ring gear 346, light beam LB from light-conducting element 306 can be directed radially outward relative to light axis LA. In examples, light axis LA can be parallel to one or both of the central axis of conducting element 306 and the central axis of sliding structure 330. In examples, light beam LB can be perpendicular to light axis LA, but can additionally be reflected at other angles. As such, light projected or emitted from light-bending element 308 can be discharged in radial directions that face away from, or are otherwise outside of, the field of view of imaging sensor 350. For example, light-bending element 308 can discharge light in the opposite direction of side-viewing imaging sensors or proximally of end-viewing imaging sensors. Thus, OCT imaging obtained from light emitted from light-bending element 308 can be used to find target tissue in blind spots of imaging sensor 350. Motor 347 can be configured to rotate lens 348 clock-wise or counter-clock-wise. As can be seen in FIG. 6, light-bending element 308 is oriented so the mirror surface is pointed upward relative to FIG. 6. However, as can be seen in FIG. 7, light-bending element 308 is rotated, either in a clock-wise or anti-clockwise direction so that the mirror surface is pointed to the right. Light beam LB can be continuously emitted so that as light-bending element 308 rotates, light beam LB is continuously emitted in an arcuate path across anatomic tissue AT. Thus, the entirety three-hundred-sixty-degree perimeter of an anatomic duct, such as a large intestine or colon, can be imaged to generate OCT imaging.

End plate 349 can comprise a shield for lens 348 to prevent damage or scratching of lens 348. End plate 349 can additionally or alternatively be opaque to prevent light from being emitted out the distal end of OCT imaging apparatus 304. End plate 349 can comprise a polymer or rubber material to form an anti-traumatic tip. In examples, end plate 349 can be of a nosecone shape.

Figure 8:
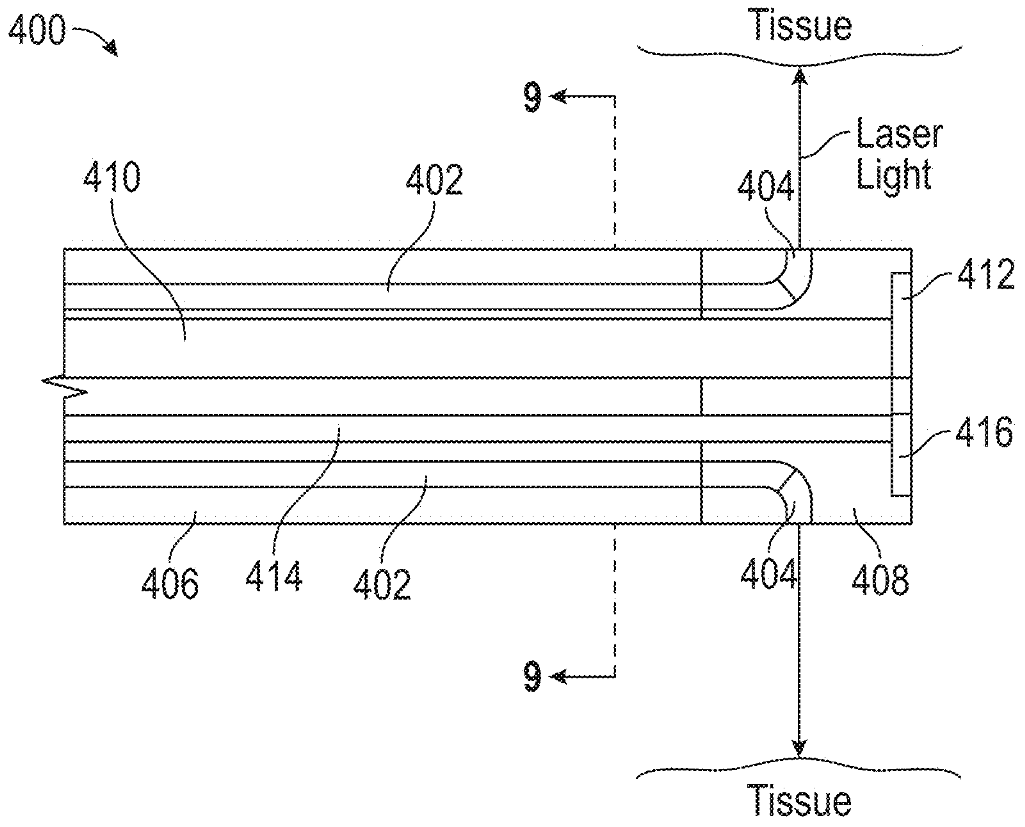
FIG. 8 is a schematic side view of an endoscope with a plurality of light conductors with radially extending emitting ends configured for performing optical imaging about the circumference of the endoscope.
Figure 9:
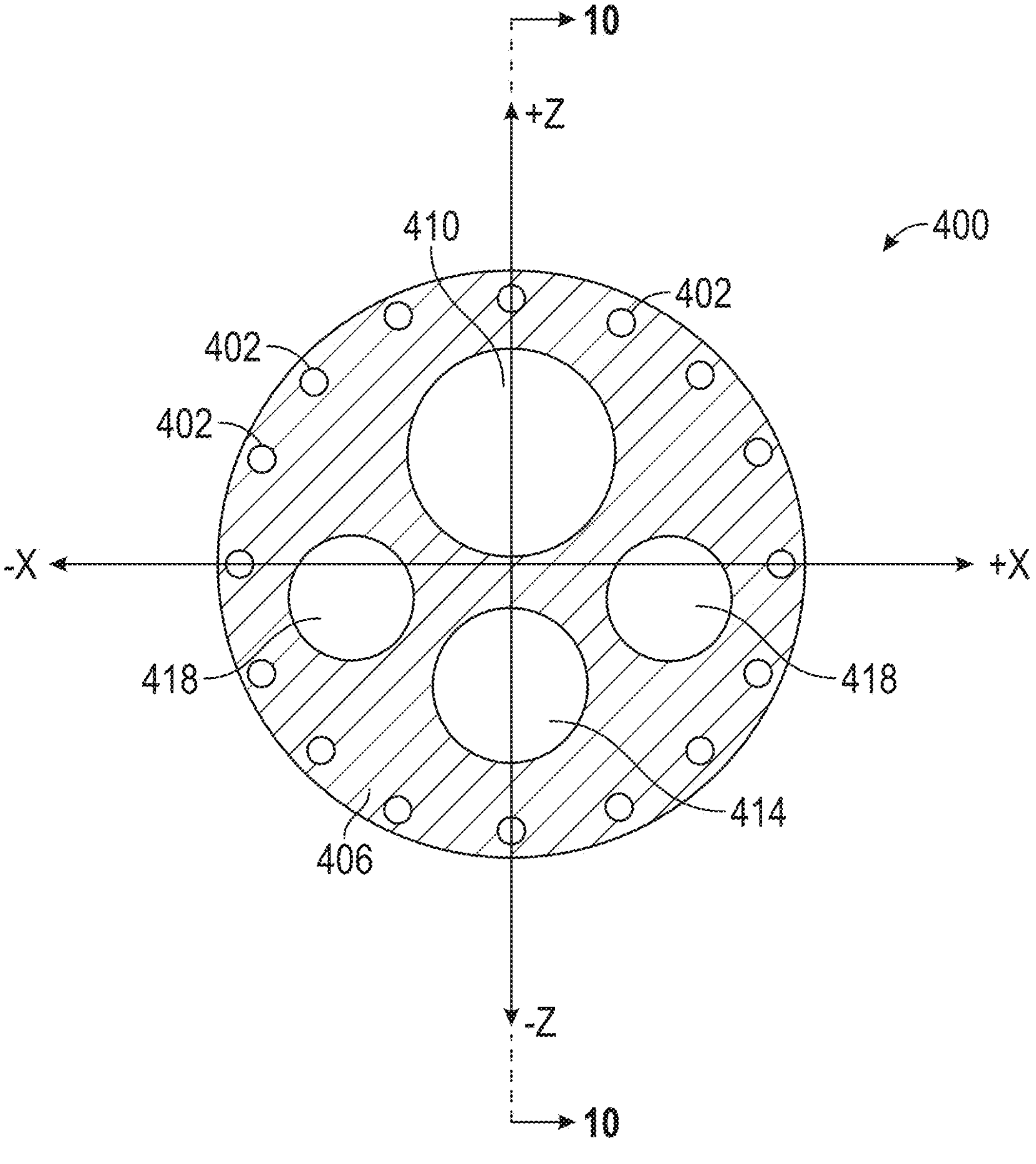
FIG. 9 is a schematic end view of the endoscope of FIG. 8 showing the plurality of light conductors disposed at different circumferential locations about the perimeter of the endoscope.

FIG. 8 is a schematic side view of endoscope 400 with a plurality of light conductors 402 with radially extending emitting ends 404 configured for performing three-hundred-sixty-degree optical coherence tomography. FIG. 9 is a schematic end view of endoscope 400 of FIG. 8 showing the plurality of light conductors 402 disposed at different circumferential locations about the perimeter of endoscope 400. Endoscope 400 can comprise elongate shaft 406, cap 408, imaging cable 410, imaging sensor 412, light cable 414, light emitter 416 and working channels 418. FIGS. 8 and 9 are discussed concurrently.

Elongate shaft 406 can be configured as an endoscope shaft. Imaging sensor 412 and light emitter 416 can be used to obtain video imaging signals that can be displayed on monitor 106, for example. Elongate shaft 406 can include one or more working channels 418 through which other devices, such as tissue removal devices, or other capabilities, such as insufflation, lavage and irrigation, can be provided. A tissue removal device can be used to remove target tissue, such as diseased tissue or pre-diseased tissue.

Endoscope 400 can also be used to obtain optical imaging, including OCT imaging, to supplement the video imaging. Endoscope 400 can be configured to emit OCT imaging light in a plurality of circumferential directions. In the illustrated example, as can be seen in FIG. 9, endoscope can include 16 light conductors 402 spaced at regular intervals around the circumference of elongate shaft 406. However, in other examples, endoscope 400 can include fewer or more light conductors 402, such as eight, twelve, sixteen, twenty, thirty-two, thirty-six or forty light conductors. As mentioned previously, the diameters of light conductors 402 can be small to occupy a small amount of space within elongate shaft 406. Light conductors 402 can be positioned close to the outer perimeter of elongate shaft 406 to provide space in the interior of elongate shaft 406 for imaging, illumination, treatment and instrumentation capabilities. As can be seen in FIG. 8, light conductors 402 can be shaped to redirect axially extending light within conductors 402 to radially extending light in radially extending emitting ends 404. Radially extending emitting ends 404 are illustrated as being positioned proximally of imaging sensor 412. However, radially extending emitting ends 404 can be positioned distally of imaging sensor 412. In examples, imaging sensor 412 can be configured with a field of view, such as in a distal direction for end-viewing, and at least some of radially extending emitting ends 404 can be oriented to project light outside of the field of view, such as in multiple radial directions proximal of the field of view. However, imaging sensor 412 can be configured in a side-viewing orientation and at least some of radially extending emitting ends 404 can be oriented to project light outside of the field of view of a side-viewing imaging sensor. In the illustrated example, radially extending emitting ends 404 extend ninety degrees relative to light conductors 402. However, in other examples, radially extending emitting ends 404 can extend less than or greater than ninety degrees, that is, at an ordinary angle relative to light conductors 402, for example, in a range of from five to one hundred seventy-five degrees relative to light conductors 402. Radially extending emitting ends 404 can comprise portions of light conductors 402 that are curved, which shaped can be achieved such as by a heating and turning process or by being molded in such shape. In examples, radially extending emitting ends 404 can be formed by abutting straight segments of light conducting material to abut mating surfaces of light conductors 402. For example, the distal ends of light conductors 402 and the proximal ends of radially extending emitting ends 404 can be chamfered at forty-five or ninety-degrees to form planar surfaces that can be abutted to conduct light. Each of light conductors 402 can be connected to a light source, such as light source device 104 (FIG. 1). The light source can be controlled, such as by controller, such as control section 133 (FIG. 3) to direct light through one or more of light conductors 402. In examples, the controller can direct light through one of light conductors 402 at a time, which neighboring light conductors 402 receiving subsequent bursts of light. Thus, light can be directed in a plurality of radial directions around the perimeter of endoscope 400, with more light conductors 402 used, greater the density of radial light bursts around the three-hundred-sixty-degree perimeter of endoscope 400. As such, optical imaging, such as OCT imaging, can be obtained about the perimeter of endoscope 400 to facilitate colonoscopy procedures. As such, light projected or emitted from light conductors 402 can be discharged in radial directions that face away from, or are otherwise outside of, the field of view of imaging sensor 412. For example, light conductors 402 can discharge light in the opposite direction of side-viewing imaging sensors or proximally of end-viewing imaging sensors. Thus, optical imaging, including OCT imaging, obtained from light emitted from light conductors 402 can be used to find target tissue in blind spots of imaging sensor 412.

FIG. 10 is a schematic view of optical tomographic imaging system 501 comprising low coherence light beam source 502. In examples, optical tomographic imaging system 501 can comprise OCT system 322 of FIGS. 1 and 3. Low coherence light beam source 502 can generate low coherence light beam whose wavelength is, for example, 1300 nm and whose coherence length is, for example, about 17 μm, that is, low coherence light beam that exhibits coherence within a short distance. For example, assume that the light beam is bisected and then merged again. If a difference between two optical path lengths to a point of bisection is a short distance of about 17 μm, the light is detected as coherent light beam. If the difference exceeds about 17 μm, the light exhibits incoherence.

Light emanating from the low coherence light beam source 502 can be incident on one end of first single-mode fiber 503*a* and propagated to the other end thereof. First single-mode fiber 503*a* can be optically coupled with second single-mode fiber 505*a* within optical coupler 504. Optical coupler 504 can bisect light into a measurement light beam and reference light. The measurement light beam can be transmitted to third single-mode fiber 503*b*, while the reference light is transmitted to fourth single-mode fiber 505*b*.

The distal end of third single-mode fiber 503*b* (coupled to the optical coupler 504) can be joined with fifth single-mode fiber 508 via optical rotary joint 507, which can include non-rotating and rotating sections and passes light, within optical imaging observation device 506. Attachment 510, or connector, of optical probe 509, which can comprise an optical scanner probe, can be freely detachably attached to the distal end of fifth single-mode fiber 508. The light emanating from low coherence light beam source 502 can be transmitted to sixth single-mode fiber 511 that can run through optical probe 509. The transmitted measurement light beam can be reflected from prism 543 incorporated in the distal part of optical probe 509, and irradiated to living-body tissue 512, e.g., the observable portions of patient Pa, that is an object while being scanned.

Moreover, the reference light separated by optical coupler 504 and propagated along fourth single-mode fiber 505*b* can be transmitted to optical path length scanning unit 513 that can change the optical path length of the reference light.

The reference light is irradiated to mirror 515 via lens 514 from the distal end surface of fourth single-mode fiber 505*b* within optical path length scanning unit 513, and then reflected from it. Mirror 515 can be advanced or withdrawn in optical-axis directions by means of actuator 516. By changing the position of mirror 515, the optical path length (optical delay) can be varied.

The action of actuator 516 can be controlled by actuator control circuit 517 connected to computer 518. Optical path length scanning unit 513 can change with high speed the optical path length of the reference light within the scanning range by optical probe 509, in relative to a predetermined scanning range extending in the direction of depth of living-body tissue 512.

Moreover, part of the measurement light beam scattered or reflected from the surface of living-body tissue 512 or internally thereof is fetched into optical probe 509 and returned to third single-mode fiber 503*b* by reversely tracing the light path. Moreover, the reference return light from optical path length scanning unit 513 returns to fourth single-mode fiber 505*b*. The return light of the measurement light beam and the reference light interfere with each other within optical coupler 504, and the resultant light is incident on photo-detector 519 through the distal end of second single-mode fiber 505*a*.

A coherence electric signal resulting from photoelectric conversion performed by photo-detector 519 is inputted to signal processing circuit 521. Signal processing circuit 521 can process the coherence electric signal. The output of signal processing circuit 521 can be transmitted to computer 518 via A/D converter 522. Computer 518 can produce image data representing a tomographic image, and transmits the image data to monitor 523, which can comprise monitor 106. Consequently, OCT image 530, image produced by optical imaging, can be displayed on display surface 523*a* of monitor 523.

Incidentally, optical rotary joint 507 can be driven by drive unit 524 included in optical imaging observation device 506.

Drive unit 524 can include rotational driving means 525 that rotationally drives the rotor included in optical rotary joint 507, and advancing/withdrawing means 527 that advances or withdraws optical rotary joint 507 and rotational driving means 525, which can be mounted on lock mount 526, in axial directions. Rotational driving means 525 and advancing/withdrawing means 527 can be controlled by driving control circuit 528.

A light guide member, e.g., hollow flexible shaft 529 with sixth single-mode fiber 511 running through it, can be included in optical probe 509 and joined with the rotor included in optical rotary joint 507 radially rotates or linearly advances or withdraws within sheath 531 of optical probe 509.

Rotational driving means 525 can consist of motor 532 that rotates for driving, motor rotor 533, which can comprise a pulley, fixed to the rotation shaft of motor 532, and belt 534 laid over between motor rotor 533 and shaft 520 through which fifth single-mode fiber 508 runs.

Advancing/withdrawing means 527 can consist of motor 535 that rotates for driving, rotary plate 536, which can be rotated by motor 535, and driving rod 537, with one end thereof coupled to rotary plate 536, and another end thereof coupled to lock mount 526, and being used to advance or withdraw the assemblage coupled to the other end thereof.

Moreover, computer 518 controls rotational driving means 525 and advancing/withdrawing means 527, which are included in drive unit 524, via driving control circuit 528.

Probe information specifying means 538 that specifies feature information concerning optical probe 509 can be connected to computer 518. Probe information specifying means 538 can be used to enter the feature information of optical probe 509, whereby computer 518 can control or perform adjustment or adjustment suitable to optical probe 509. Probe information specifying means 538 is a kind of manual input means, for example, a keyboard or switches.

Alternatively, probe information specifying means 538 can be replaced with means for automatically detecting the feature information of optical probe 509 as described later.

For brevity's sake, FIG. 10 shows the means for automatically detecting the feature information of optical probe 509 together with probe information specifying means 538.

As shown in FIG. 10, optical probe 509 is connected to optical imaging observation device 506 via attachment 510 of optical probe 509. Probe information holding means 539 is incorporated in attachment 510 of optical probe 509.

Probe information detecting means 540 can be provided opposite probe information holding means 539 and located in the portion of optical imaging observation device 506 coupled to attachment 510 of optical probe 509. Owing to this structure, when optical probe 509 is connected to optical imaging observation device 506, probe information held in probe information specifying means 538 can be detected by probe information detecting means 540 and inputted thereto. The probe information is then transmitted to computer 518. Computer 518 can check the detected probe information, and controls the system or determines the settings of the system according to optical probe 509.

In examples, optical tomographic imaging system 501 can be configured according to U.S. Pat. No. 7,072,046 B2 to Xie, titled "Optical imaging system and optical imaging detection method," the entire contents of which are hereby incorporated by this reference.

Optical probe 509 of optical tomographic imaging system 501 can incorporate the features of endoscope 300 of FIG. 4 or endoscope 400 of FIG. 8. That is, optical probe 509 can be configured to obtain three-hundred-sixty-degree OCT imaging signals according to the present disclosure to facilitate identification and finding of target tissue. Optical probe 509 can be integrated into endoscope 102 of endoscope system 101 of FIG. 1. As such, a video imaging endoscope can be integrated with OCT imaging capabilities that can obtain OCT image signals about the circumference of the endoscope in a plurality of discrete locations or in a continuous imaging band.

Figure 11:
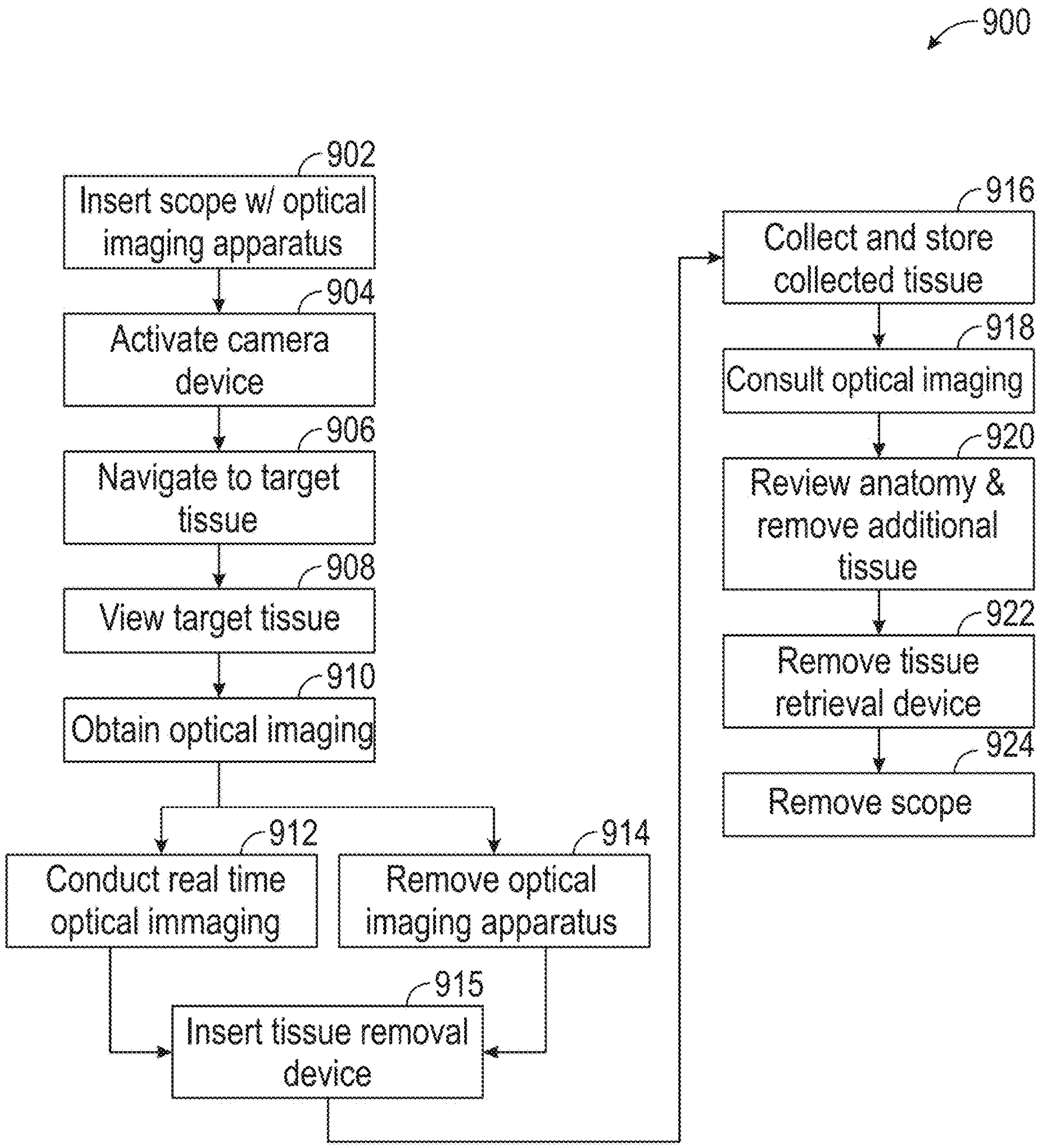
FIG. 11 is block diagram illustrating methods of obtaining optical imaging using an endoscope and performing a colonoscopy procedure according to the present disclosure.

FIG. 11 is block diagram illustrating method 900 of obtaining optical imaging, such as Optical Coherence Tomography (OCT) imaging, using an endoscope and performing a colonoscopy procedure according to the present disclosure. Method 900 can encompass the use of endoscope 300 of FIG. 4, as well as other instruments. Method 900 can additionally be used with the devices and systems of FIGS. 2-3 and 10. Method 900 can comprise operation 902-operation 924 and can describe various procedures for obtaining three-hundred-sixty-degree optical imaging from an endoscope. In various examples, additional operations consistent with the devices, systems methods and operations described herein can be included. Likewise, some of operation 902-operation 924 can be omitted. Additionally, operations 902-operation 924 can be performed in other sequences.

At operation 902, an endoscope, such as a colonoscope, can be inserted into and navigated through anatomy of a patient. For example, endoscope 300 (FIG. 4) can utilize imaging capabilities, e.g., video imaging, to guide elongate body 302 through anatomic ducts of the patient. In examples, the endoscope can be introduced into the anus and guided through the large intestine to the colon. Elongate body 302 can be bent or curved using controller 310 and appropriate steering wires to facilitate turning of endoscope 300.

At operation 904, a camera device can be activated. For example, image acquisition section 131 and image sensor 115 (FIG. 1) or imaging sensor 350 (FIG. 5) can be activated to obtain video imaging that can be displayed on monitor 106. A surgeon can view the video images to guide the endoscope to the desired anatomy.

At operation 906, the endoscope can be navigated to the location of target tissue within the patient. The target tissue can comprise tissue that is diseased, potentially diseased or otherwise indicative of a diseased condition of the patient. The target tissue can comprise tissue that is cancerous or pre-cancerous tissue, within the anatomy. In examples, endoscope 300 (FIG. 4) can be inserted into a colon of the patient to identify and remove cancer polyps.

At operation 908, the camera device can be utilized to view the target tissue via a video image feed. The target tissue can be analyzed for the identification of tissue to be removed. For example, a surgeon can view the video image feed to determine the location of cancer polyps for removal. The target tissue can be viewed using monitor 106 in real time. Light from a light source can be used to illuminate the target tissue. For example, light from light source 142 (FIG. 3) or illumination lenses 352 (FIG. 5) can be directed upon the target tissue.

At operation 910, optical imaging, such as Optical Coherence Tomography (OCT) imaging, can be obtained from the endoscope. For example, OCT imaging apparatus 304 or another imaging apparatus such as a photoacoustic imaging apparatus, a diffuse optical tomography (DOT) apparatus, a Raman spectroscopy apparatus, a super-resolution microscopy apparatus and the like, can be used to obtain optical imaging of the anatomy. The optical imaging can be displayed on monitor 106 and/or monitor 523. The optical imaging can be obtained from a plurality of circumferential directions relative to the central axis of the endoscope. In examples, a continuous three-hundred-sixty-degree ring of optical imaging can be obtained, such as by using rotating light-bending element 308. In examples, optical imaging can be obtained at intervals about a three-hundred-sixty-degree perimeter of the endoscope, such as at one-degree intervals, five-degree intervals, ten-degree intervals, fifteen-degree intervals or wider intervals, such as by using light conductors 402. The optical imaging can be obtained outside of the field of view of the camera device used at operations 904 to 908. In examples, the optical imaging can be obtained proximally or distally of images obtained by the camera device or on opposite sides of the insertion shaft of the endoscope. In examples, optical imaging can be obtained and saved, such as in computer memory, for viewing after optical imaging is ceased. The obtained optical imaging can be later referenced, such as by comparing pre-operative optical imaging to post-operative optical imaging or for guiding a tissue retrieval device to areas of interest in the optical imaging.

At operation 912, real-time optical imaging can be obtained. The real-time optical imaging can be used by a surgeon to direct the endoscope to locations within the anatomy where target tissue is located that were not visible with only the video imaging. Additionally, the real-time optical imaging can be used by the surgeon to verify that the target tissue treated with the video imaging is addressed, i.e., treated, all of the target tissue. In other words, the optical imaging can be used to cross-check the video imaging.

At operation 914, the optical capability can be removed from the endoscope to allow for the insertion of another instrument. For example, optical imaging apparatus 304 can be removed from elongate body 302, such as by sliding structure 330 out of lumen 316.

At operation 915, a tissue removal device or biopsy forceps can be extended from the endoscope to engage target tissue. In examples, the tissue removal device can be passed through an open lumen within the endoscope. The open lumen can comprise a dedicated working channel not used for video or optical imaging. The lumen can alternatively comprise a lumen used to temporarily receive optical imaging apparatus 304.

At operation 916, the tissue collection device can be pushed, pressed or otherwise brought into pressurized contact with the target tissue. For example, the tissue collection device can be reciprocated axially, or rotated, to cause teeth or cutting elements to slice, punch or shave, etc. one or more pieces of tissue away from the anatomy of the patient. Sample tissue or biological matter separated or collected from the patient at operation 916 can be stored within a space inside the tissue collection device.

At operation 918, the optical imaging can be consulted. For example, if real-time OCT imaging is used at operation 912, the optical imaging can be used to help guide the endoscope and the tissue retrieval device disposed therein to target tissue. The real-time optical imaging can be reviewed to look for target tissue, e.g., cancer polyps, not visible in the camera or video imaging. If previously recorded optical imaging is used, target tissue identified in the recorded optical imaging can be compared to results of the tissue removal process to verify all areas of interest in the recorded optical imaging have been removed.

At operation 920, the anatomy can be reviewed by moving the endoscope to locations identified at operation 918 to permit additional review and tissue removal. For example, operation 918 and operation 920 may indicate that some target tissue identified in the optical imaging still remain in the anatomy. Thus, tissue removal procedures at operation 916 can be repeated.

At operation 922, the tissue collection device can be removed from the patient, such as by removal from the endoscope, which can be left in the anatomy. After the optical imaging is used to verify that all target tissue of interest has been removed an no further target tissue can be identified with video imaging or optical imaging, the tissue collection device can be removed. The collected sample tissue can be removed from the tissue collection device.

At operation 924, the endoscope can be removed from the patient. The patient can thereafter be appropriately prepared for completion of the procedure.

As such, method 900 illustrates examples of a method of collecting biological matter from internal passages of a patient using multi-directional optical imaging signals to gain views of an anatomic duct distributed about the perimeter of the duct. The optical imaging can provide a complete three-hundred-sixty-degree view of the duct or a view of the perimeter of the duct at a plurality of circumferential images. The optical imaging can be used to view obstructed tissue that can be difficult to view using conventional video imaging.

EXAMPLES

Example 1 is an endoscope comprising: an elongate shaft extending along an axis from a proximal end portion to a distal end portion; a video imaging device located in the distal end portion, the video imaging device including a field of view; and an optical coherence tomography (OCT) imaging system configured to emit light outside of the field of view.

In Example 2, the subject matter of Example 1 optionally includes wherein the OCT imaging system is configured to emit light in multiple radial directions relative to the axis.

In Example 3, the subject matter of any one or more of Examples 1-2 optionally include wherein the OCT imaging system comprises: a light conductor extending at least partially through the elongate shaft.

In Example 4, the subject matter of Example 3 optionally includes wherein the OCT imaging system further comprises: a mirror rotatably mounted at the distal end portion to direct light from the light conductor radially outward relative to the axis.

In Example 5, the subject matter of Example 4 optionally includes wherein the mirror is within a lens and may be partially or fully surrounded by the lens.

In Example 6, the subject matter of Example 5 optionally includes wherein the mirror comprises a prism disposed within the lens.

In Example 7, the subject matter of any one or more of Examples 5-6 optionally include wherein the lens is disposed distally of a distal end face of the elongate shaft.

In Example 8, the subject matter of any one or more of Examples 5-7 optionally include wherein the elongate shaft comprises: a working channel extending at least partially through the elongate shaft to the distal end portion.

In Example 9, the subject matter of Example 8 optionally includes wherein the light conductor extends through the working channel.

In Example 10, the subject matter of Example 9 optionally includes wherein the lens includes an outer diameter that is less than an outer diameter of the working channel.

In Example 11, the subject matter of any one or more of Examples 9-10 optionally include wherein the light conductor is encased in a support structure.

In Example 12, the subject matter of Example 11 optionally includes wherein the support structure is removable from the working channel.

In Example 13, the subject matter of any one or more of Examples 5-12 optionally include a motor connected to the lens to provide rotation of the lens about the axis.

In Example 14, the subject matter of Example 13 optionally includes wherein the lens is connected to a ring gear and the motor is connected to a pinion gear.

In Example 15, the subject matter of any one or more of Examples 3-14 optionally include wherein the light conductor includes an inflection to orient a light-emitting face radially outward relative to the axis.

In Example 16, the subject matter of Example 15 optionally includes wherein an axis of the light-emitting face is tangential to the axis of the elongate shaft.

In Example 17, the subject matter of any one or more of Examples 15-16 optionally include wherein the light conductor is one of a plurality of light conductors extending through the elongate shaft configured to emit light radially relative to the axis of the elongate shaft.

In Example 18, the subject matter of Example 17 optionally includes each light conductor of the plurality of light conductors with a diameter in the range of approximately 50 microns to 150 microns.

In Example 19, the subject matter of any one or more of Examples 17-18 optionally include wherein the plurality of light conductors includes twenty or more light conductors.

In Example 20, the subject matter of any one or more of Examples 17-19 optionally include wherein the plurality of light conductors are spaced at intervals in the range of approximately five degrees to approximately fifteen degrees.

In Example 21, the subject matter of any one or more of Examples 17-20 optionally include a controller configured to selectively direct a light beam through each of the plurality of light conductors.

In Example 22, the subject matter of any one or more of Examples 1-21 optionally include wherein the video imaging device is located distal of the OCT imaging system.

In Example 23, the subject matter of any one or more of Examples 1-22 optionally include wherein: The video imaging device includes a first field of view; and the OCT imaging system includes a second field of view; wherein the second field of view is proximal of the first field of view.

Example 24 is a method of imaging anatomy using an endoscope, the method comprising: inserting the endoscope into anatomy of a patient, the endoscope comprising an elongate body with a central axis; obtaining imaging with a video imaging device that includes a field of view; emitting light from a distal end portion of the endoscope outside of the field of view; obtaining reflected light from the emitted light; and generating optical coherence tomography images of the anatomy from the reflected light.

In Example 25, the subject matter of Example 24 optionally includes wherein emitting light from the distal end portion of the endoscope comprises emitting light in multiple radial directions relative to the central axis.

In Example 26, the subject matter of any one or more of Examples 24-25 optionally include simultaneously generating the optical coherence tomography images of the anatomy and video images of the anatomy.

In Example 27, the subject matter of Example 26 optionally includes identifying target tissue with the optical coherence tomography images that is not visible in the video images.

In Example 28, the subject matter of any one or more of Examples 24-27 optionally include wherein emitting the light from a distal end portion of the endoscope in multiple radial directions relative to the central axis comprises deflecting a light beam in the multiple radial directions.

In Example 29, the subject matter of Example 28 optionally includes wherein deflecting the light beam in the multiple radial directions comprises: directing light through a light conductor extending along a light axis; and rotating a light-deflector located distal of the light conductor about the light axis.

In Example 30, the subject matter of Example 29 wherein rotating the light-deflector located distal of the light conductor about the light axis optionally comprises rotating a prism that includes a reflecting surface angled between zero and one hundred eighty degrees (ordinary angle) to the light axis, including forty-five and ninety degrees, to the light axis.

In Example 31, the subject matter of any one or more of Examples 29-30 optionally include removing the light conductor and the light-deflector from a working channel of the endoscope; and inserting a tissue removal device into the working channel.

In Example 32, the subject matter of any one or more of Examples 28-31 optionally include wherein emitting a light beam from a distal end portion of the endoscope in multiple radial directions relative to the central axis comprises: directing light through a plurality of light conductors extending along light axes extending parallel to a central axis of the endoscope; and turning light extending through the plurality of light conductors at distal ends of the plurality of light conductors between zero and one hundred eighty degrees (ordinary angle) to the light axis, including forty-five and ninety degrees, to project radially outward relative to the central axis.

In Example 33, the subject matter of Example 32 optionally includes pulsing light through one of the plurality of light conductors at a time in a circumferential direction.

In Example 34, the subject matter of any one or more of Examples 24-33 optionally include wherein the video imaging device is located distally of where the light is emitted from the distal end portion of the endoscope outside of the field of view.

In Example 35, the subject matter of any one or more of Examples 24-34 optionally include wherein: the video imaging device includes a field of view; and the light is emitted from the distal end portion of the endoscope outside of the field of view.

Example 36 is an image processing system for an endoscopy system with optical coherence tomography (OCT) capabilities for generating OCT images of anatomy, the image processing system comprising: an image processor configured to: receive image data from a video imaging device associated with the endoscopy system, the video imaging device including a field of view; receive OCT data from an OCT device associated with the endoscopy system; and generate an imaging signal for displaying an OCT image for anatomy outside of the field of view of the video imaging device.

In Example 37, the subject matter of Example 36 optionally includes D images from the OCT data for anatomy outside of the field of view of the video imaging device.

In Example 38, the subject matter of any one or more of Examples 36-37 optionally include wherein the image processor is configured to: generate video images from the image data of the video imaging device; and generate OCT images from the OCT data for a blind spot within the video images.

In Example 39, the subject matter of any one or more of Examples 36-38 optionally include wherein the image processor is configured to assemble OCT images for OCT data obtained at different radial positions relative an endoscope shaft of the endoscopy system.

In Example 40, the subject matter of any one or more of Examples 36-39 optionally include a video monitor on which the OCT image can be displayed.

Each of these non-limiting examples can stand on its own, or can be combined in various permutations or combinations with one or more of the other examples.

Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72 (b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. An endoscope comprising:

an elongate shaft extending along an axis from a proximal end portion to a distal end portion;

a video imaging device located in the distal end portion, the video imaging device including a field of view configured to view distally of the elongate shaft; and an optical imaging system configured to emit light in a radial direction and collect reflected light from anatomy to independently generate depth-resolved optical images of the anatomy about a circumference of the elongate shaft outside of the field of view of the video imaging device, wherein the optical imaging system includes radially extending emitting ends positioned proximally of the video imaging device.

2. The endoscope of claim 1, wherein the optical imaging system is configured to emit light in multiple radial directions relative to the axis.

3. The endoscope of claim 1, wherein the optical imaging system comprises:

a light conductor extending within the elongate shaft.

4. The endoscope of claim 3, wherein:

the elongate shaft comprises an imaging cable, a light cable and a working channel extending through an interior of the elongate shaft;

the light conductor is one of a plurality of light conductors extending through the elongate shaft, each light conductor configured to emit light radially relative to the axis of the elongate shaft; and each of the plurality of light conductors are arranged in different circumferential positions within the elongate shaft surrounding the imaging cable, the light cable and the working channel.

5. The endoscope of claim 4, wherein:

each of the plurality of light conductors includes an inflection to orient a light-emitting face of each light conductor radially outward relative to the axis; and a central axis of each of the light-emitting faces is tangential to the axis of the elongate shaft.

6. The endoscope of claim 5, wherein the video imaging device is located distal of the inflections of the plurality of light conductors of the optical imaging system.

7. The endoscope of claim 4, wherein:

each light conductor of the plurality of light conductors includes a diameter in the range of 50 microns to 150 microns;

wherein the plurality of light conductors includes at least twenty light conductors; and wherein the plurality of light conductors are spaced at intervals in the range of five degrees to fifteen degrees.

8. The endoscope of claim 4, further comprising a controller configured to selectively direct a light beam through each of the plurality of light conductors one at a time, with neighboring light conductors receiving subsequent light bursts.

9. The endoscope of claim 4, wherein each of the plurality of light conductors comprises an optical fiber extending from the distal end portion, through the elongate shaft and to a controller of the endoscope.

10. The endoscope of claim 1, wherein:

the field of view of the video imaging device comprises a first field of view; and the optical imaging system includes a second field of view;

wherein the second field of view is proximal of the first field of view.

11. A method of imaging anatomy using an endoscope, the method comprising:

inserting the endoscope into anatomy of a patient, the endoscope comprising an elongate body with a central axis;

obtaining imaging with a video imaging device that includes a field of view oriented distally of the elongate body;

emitting light from a distal end portion of the endoscope in a radial direction about a circumference of the elongate body outside and proximal of the field of view;

obtaining reflected light from the emitted light; and generating depth-resolved optical images of the anatomy from the reflected light.

12. The method of claim 11, wherein emitting light from the distal end portion of the endoscope comprises emitting light in multiple radial directions relative to the central axis.

13. The method of claim 11, further comprising:

simultaneously generating the depth-resolved optical images of the anatomy and video images of the anatomy; and identifying target tissue with the depth-resolved optical images that is not visible in the video images.

14. The method of claim 11, wherein emitting the light from a distal end portion of the endoscope in multiple radial directions relative to the central axis comprises deflecting a light beam in the multiple radial directions, wherein deflecting the light beam in the multiple radial directions comprises:

directing light through a light conductor extending along a light axis; and rotating a light-deflector located distal of the light conductor about the light axis, wherein rotating the light-deflector located distal of the light conductor about the light axis comprises rotating a prism that includes a reflecting surface at an ordinary angle to the light axis.

15. The method of claim 14, further comprising:

removing the light conductor and the light-deflector from a working channel of the endoscope; and inserting a tissue removal device into the working channel.

16. The method of claim 14, wherein emitting a light beam from a distal end portion of the endoscope in multiple radial directions relative to the central axis comprises:

directing light through a plurality of light conductors extending along light axes extending parallel to a central axis of the endoscope; and turning light extending through the plurality of light conductors at distal ends of the plurality of light conductors at an ordinary angle to project radially outward relative to the central axis.

17. The method of claim 16, further comprising pulsing light through one of the plurality of light conductors at a time in a circumferential direction.

18. The method of claim 11, wherein the video imaging device is located distally of where the light is emitted from the distal end portion of the endoscope outside of the field of view.

19. The method of claim 11, wherein:

the video imaging device includes a field of view; and the light is emitted from the distal end portion of the endoscope outside of the field of view.

20. An endoscope comprising:

an elongate shaft extending along an axis from a proximal end portion to a distal end portion, the elongate shaft comprising an imaging cable, a light cable and a working channel extending through an interior of the elongate shaft;

a video imaging device located in the distal end portion, the video imaging device connected to the imaging cable and including a field of view configured to view distally of the elongate shaft; and an optical imaging system comprising:

an elongate structure insertable into the working channel so as to protrude through a distal end of the elongate shaft;

an optical fiber extending through the elongate structure and configured to transmit light for depth-resolved optical imaging;

a cap rotatably connected to the elongate structure and positioned proximally of the video imaging device; and a mirror positioned within the cap to receive light emitted from the optical fiber and reflect the light radially outward of the elongate structure outside of the field of view of the video imaging device.

21. The endoscope of claim 20, wherein the cap comprises a lens fabricated of transparent material and the mirror is within the lens.

22. The endoscope of claim 21, wherein the mirror comprises a prism disposed within the lens.

23. The endoscope of claim 21, wherein the lens is disposed distally of a distal end face of the elongate shaft.

24. The endoscope of claim 20, further comprising:

a drive shaft extending through the elongate shaft;

a pinion gear disposed at an end of the drive shaft;

a motor connected to the drive shaft to induce rotation of the drive shaft; and a ring gear coupled to the cap such that rotation of the motor causes the that-cap to rotate via the drive shaft and pinion gear.

* * * * *